United States Patent
Heiss-Chouquet et al.

(10) Patent No.: US 9,784,655 B2
(45) Date of Patent: Oct. 10, 2017

(54) METHOD AND APPARATUS FOR DETERMINING THE FRACTURE STRENGTH OF THE MARGINS OF THIN SHEETS OF BRITTLE-FRACTURE MATERIAL

(71) Applicant: SCHOTT AG, Mainz (DE)

(72) Inventors: Markus Heiss-Chouquet, Bischofsheim (DE); Kurt Nattermann, Ockenheim (DE); Clemens Ottermann, Hattersheim (DE); Matthias Jotz, Alfeld (DE)

(73) Assignee: SCHOTT AG, Mainz (DE)

( * ) Notice: Subject to any disclaimer, the term of this patent is extended or adjusted under 35 U.S.C. 154(b) by 75 days.

(21) Appl. No.: 14/814,536

(22) Filed: Jul. 31, 2015

(65) Prior Publication Data
US 2016/0033379 A1    Feb. 4, 2016

(30) Foreign Application Priority Data

Jul. 31, 2014 (DE) .......................... 10 2014 110 855

(51) Int. Cl.
*G01N 3/08* (2006.01)
*G01N 3/20* (2006.01)

(52) U.S. Cl.
CPC ............. *G01N 3/08* (2013.01); *G01N 3/20* (2013.01); *G01N 2203/0017* (2013.01); *G01N 2203/0067* (2013.01); *G01N 2203/028* (2013.01); *G01N 2203/0278* (2013.01)

(58) Field of Classification Search
CPC ... G01N 3/10; G01N 3/08; G01N 3/20; B32B 17/00

USPC .......................................................... 73/834
See application file for complete search history.

(56) References Cited

U.S. PATENT DOCUMENTS

| | | | |
|---|---|---|---|
| 3,983,745 A | 10/1976 | Juusola | |
| 4,003,246 A | 1/1977 | Cain | |
| 4,753,115 A | 6/1988 | Moody | |
| 4,823,609 A | 4/1989 | Yost | |
| 4,899,507 A * | 2/1990 | Mairlot | ............. B32B 17/10036 52/204.5 |
| 4,916,954 A | 4/1990 | Buzzard | |
| 5,054,324 A | 10/1991 | Pohl | |

(Continued)

FOREIGN PATENT DOCUMENTS

| | | |
|---|---|---|
| AT | 411714 B | 4/2004 |
| DE | 141571 | 5/1980 |

(Continued)

OTHER PUBLICATIONS

English translation of Nattermann et al.: "Bruchstatistik" [Fracture Statistics] in "Festigkeit von Glas—Grundlagen and Messverfahren" [Strength of Glass—Basics and Methods of Measurement], ISBN3-921089-30-1, 11 pages.

(Continued)

*Primary Examiner* — Lisa Caputo
*Assistant Examiner* — Octavia Hollington
(74) *Attorney, Agent, or Firm* — Ohlandt, Greeley, Ruggiero & Perle, L.L.P.

(57) ABSTRACT

A method and an apparatus for examining the fracture strength of flat samples made of brittle-fracture material are provided. The margin of the respective sample is subjected to tensile stress by bending the material in a circular arc shape.

22 Claims, 8 Drawing Sheets

(56) References Cited

U.S. PATENT DOCUMENTS

| | | | |
|---|---|---|---|
| 5,431,062 A | 7/1995 | Baratta | |
| 5,437,192 A | 8/1995 | Kawamoto et al. | |
| 5,594,178 A | 1/1997 | Takahashi et al. | |
| 5,616,848 A * | 4/1997 | Hemingway | G01N 3/20 73/838 |
| 5,892,157 A | 4/1999 | Syre | |
| 7,461,564 B2 * | 12/2008 | Glaesemann | G01N 3/20 73/862.381 |
| 8,365,610 B2 | 2/2013 | Decraecker et al. | |
| 8,825,423 B1 | 9/2014 | Brovold | |
| 2002/0032117 A1 | 3/2002 | Peuchert et al. | |
| 2003/0076487 A1 | 4/2003 | Cannon et al. | |
| 2008/0083288 A1 | 4/2008 | Glaesemann | |
| 2013/0207058 A1 | 8/2013 | Wegener et al. | |
| 2013/0283875 A1 * | 10/2013 | Jin | B21D 5/004 72/17.3 |
| 2013/0298692 A1 | 11/2013 | Seok | |
| 2013/0319048 A1 | 12/2013 | Hartmann | |
| 2014/0069203 A1 | 3/2014 | McColskey et al. | |
| 2014/0083198 A1 | 3/2014 | Sharps et al. | |
| 2014/0352451 A1 | 12/2014 | Kismarton | |

FOREIGN PATENT DOCUMENTS

| | | |
|---|---|---|
| DE | 233187 | 2/1986 |
| DE | 69001746 | 9/1993 |
| DE | 19540891 A1 | 5/1996 |
| DE | 19637808 | 12/1997 |
| DE | 102007005671 | 8/2008 |
| DE | 102012104594 A1 | 12/2013 |
| JP | S52113789 A | 9/1977 |
| JP | S58101420 | 6/1983 |
| JP | H0378641 | 4/1991 |
| JP | H0854328 A | 2/1996 |
| JP | H1123437 A | 1/1999 |
| JP | 2000321188 A | 11/2000 |
| JP | 2001221729 A | 8/2001 |
| JP | 2004184238 | 7/2004 |
| JP | 2010506168 | 2/2010 |
| JP | 2010078325 A | 4/2010 |
| JP | 2011033376 | 2/2011 |
| JP | 2011202991 | 10/2011 |
| JP | 2012247208 | 12/2012 |
| JP | 2014002018 | 1/2014 |

OTHER PUBLICATIONS

Gulati et al., "Two Point Bending of Thin Glass Substrate", Corning Incorporated, Corning, NY, 3 pages.

* cited by examiner

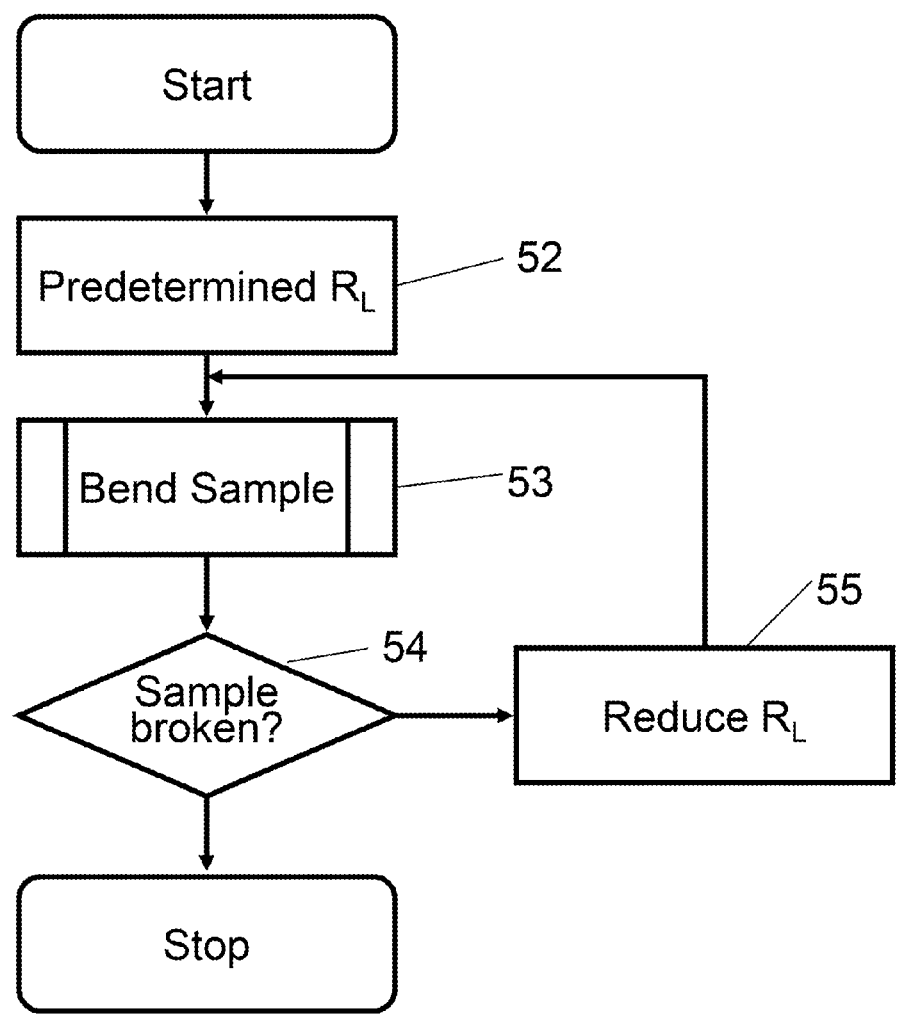

METHOD AND APPARATUS FOR DETERMINING THE FRACTURE STRENGTH OF THE MARGINS OF THIN SHEETS OF BRITTLE-FRACTURE MATERIAL

CROSS REFERENCE TO RELATED APPLICATIONS

This application claims benefit under 35 U.S.C. §119(a) of German Patent Application No. DE 10 2014 110 855.8 filed Jul. 31, 2014, the entire contents of which are incorporated herein by reference.

BACKGROUND

1. Field of the Invention

The invention relates to the determination of the fracture strength of thin, flat samples of brittle-fracture material, in particular thin glass sheets, under a tensile stress $\sigma$.

2. Description of Related Art

It has been found that two mutually independent kinds of fractures can occur when such samples are placed under tensile loads: fractures that have their origin inside the surface area of the sample and those that grow starting from the margin of the sample. The present invention relates to the latter kind of fractures, that is, to those that have their origin at the margin of the sample.

Both for characterization and optimization of the properties of the edge and for ensuring a guaranteed fracture strength, it is advantageous to examine whether the margin of a sample withstands a certain tensile stress $\sigma$.

Moreover, it is advantageous to determine the stress $\sigma_b$ of such a sample, in which the sample fractures starting from the margin (tensile stress at break).

A two-point bending method is known for the determination of the tensile stress at break of thin glass samples from, for example, S. T. Gulati: "Two Point Bending of Thin Glass Substrate," SID Symposium, Techn. Papers Vol. 42, pp. 652-654 (2011). In this case, a thin glass sample is clamped between two support plates and bent by bringing these plates together (compare FIG. 1).

This method has a number of drawbacks. In this kind of bending, an inhomogeneous state of stress is created along the sample, with the highest stress being imposed along the margin in the middle of the sample and the stress declining with increasing distance from the middle. Therefore, this method is not adequate for characterizing extended sections of sample margins under a given stress. The generalization of the measured values of local tensile stress at break to larger sections with this method has been demonstrated to be reliable only to a limited extent. Moreover, samples with inhomogeneous thickness cause problems in this method, which can be solved only with difficulty. Furthermore, the necessity of clamping places requirements on the geometry of the samples and, in many cases, makes necessary a tedious preparation of the samples. In addition, the cost in terms of instruments and personnel required to carry out this method cannot be underestimated.

SUMMARY

The invention is therefore based on the object of reducing the drawbacks of the prior art. In particular, a possibility for simple and reliable examination of the fracture strength of the margins of samples under a mechanical tensile stress $\sigma$ shall be provided.

The invention is based on the realization that, when a sample is bent, the sample material is subjected to a tensile stress $\sigma$ on the outer side of the bend.

A sample that is to be characterized by the method according to the invention comprises a first lateral face and a second lateral face lying opposite to it as well as at least one margin. This margin, which is to be examined, forms a transition of the first face to the second face. It can be designed to be angular or rounded, for example, or it can comprise a border. The sample has a thickness t at this margin.

It is intended, in particular, to examine samples made of glass, preferably with a thickness of at most one millimeter, most preferably of at most 300 micrometers.

According to the invention, the margin of the sample to be examined is to be examined in terms of its fracture strength initially in the region of the first lateral face.

Accordingly, the invention comprises a method for examining the fracture strength of flat samples made of brittle-fracture material, in particular glass sheets, in which said samples have a first lateral face and a second lateral face as well as at least one margin and the first lateral face lies opposite to the second lateral face, in regard to fractures originating under a mechanical tensile stress $\sigma$ from this margin of the sample to be examined, wherein the first lateral face is subjected to a tensile stress $\sigma$ along the margin to be examined at the margin to be examined in a section of the sample by bending the sample in this section to be examined, so that said sample is imparted a bend along the margin to be examined, by pressing the sample in the section to be examined against the template surface of a dimensionally stable template of defined curvature, so that the curvature of the template surface is imposed on the section to be examined, wherein a template surface having a first bending radius R is used and the fracture strength of the sample is examined under the mechanical tensile stress $\sigma$ corresponding to this bending radius R, and this test is repeated with successively reduced bending radius R and the thereby ensuing, increased tensile stress $\sigma$ until the sample breaks, and an analysis is performed to determine the tensile stress $\sigma$ or bending radius at which the sample has fractured.

Preferably, it is also determined whether the sample has fractured starting at the margin to be examined.

This method according to the invention has a number of advantages. The position of the margin region that is bent with the bending radius R along the margin is—in contrast to the known method discussed above—not predetermined by the geometry or preparation of the sample, but rather said position can be chosen at will by placing the template against the section to be examined. The method places only very small requirements even on the preparation of the sample. Essentially, it need only be possible to be able to bend the margin in the section to be examined by means of the template. In contrast to the known method, the geometry of the other margins, which are not to be examined, does not have any significant influence on the measurement. Moreover, the measurement is simpler in terms of instruments and personnel and is less sensitive to error. Furthermore, samples of inhomogeneous thickness t can also be examined. Changes in thickness remote from the margin to be examined do not generally have any influence on the method. If the thickness t changes along the margin, the local value of the tensile stress $\sigma$ to which the respective section of the sample margin has been subjected changes; this can be reconstructed, if need be, by analyzing the respective local thickness of the margin.

Preferably, the samples are planar structures in a state free of external forces, which do not undergo any plastic deformation during the bending according to the invention, so that, after the measurement, they revert to their original geometry (unless they are broken).

The samples are preferably bent in a cylindrical manner, so that the section of the sample that has undergone bending in a circular arc shape assumes the form of at least a section of a hollow cylinder, wherein, in this cylindrically bent section of the sample, the first lateral face of the sample represents the outer lateral surface of this hollow cylinder and the second lateral face of the sample represents the inner lateral surface of this hollow cylinder and the margin of the sample to be examined runs along the base area of this hollow cylinder. Accordingly, in an especially preferred enhancement of the invention, the template surface is curved in the shape of the arc of a circle, so that, by pressing the sample against the template surface, a bend of circular arc shape having a bending radius R is imposed on it.

However, the bending need not be in a circular arc shape and it is still possible to subject the sample to a defined tensile stress by pressing it against the template surface. For example, the template surface can be parabolic or elliptical in shape. In the case of such a surface, the bending radius constantly changes and assumes a minimum value at the apex.

The method according to the invention can be applied, in particular, to thin glass samples, such as, for example, those with thicknesses t from the set {10 µm, 15 µm 20 µm, 25 µm, 30 µm, 35 µm, 40 µm, 45 µm, 50 µm, 55 µm, 65 µm, 70 µm, 75 µm, 85 µm, 100 µm, 110 µm, 120 µm, 145 µm, 160 µm, 180 µm, 200 µm, 210 µm, 250 µm}. Tensile stresses σ within a broad range are possible, such as, for example, 20 MPa, 40 MPa, 80 MPa, 100 MPa.

A preferred embodiment of the method according to the invention is characterized in that an extended section of the margin to be examined is subjected to the mechanical tensile stress σ by bending the sample section by section along the margin to be examined by advancing the sample along the margin to be examined either continuously or stepwise relative to the template, so that a successively enlarged section of the margin of the sample to be examined has been subjected to a defined bending predetermined by the shape of the template surface.

In particular, it is possible in this case for the template surface to have a homogeneous cross section of circular arc shape at least in one region and for an extended section of the sample along the margin to be examined to be pressed flat against this template region in a circular arc shape, so that an extended bend of circular arc shape with the constant bending radius R is imposed on this pressed margin section of the sample.

This embodiment makes it possible also to examine extended sections of sample margins without any gaps under a tensile stress σ that remains constant, or else up to a given tensile stress σ. This was not possible experimentally by means of the two-point bending method. Only the utilization of the template enables any position of the margin to be bent and, in particular, as provided for here according to an embodiment, to impose a bend over the margin.

This embodiment makes it possible to examine margins of nearly any length. The relative movement between the margin and the template can induce a sliding of the margin on the template. However, this sliding can also be prevented, for example, by rolling the margin on a cylindrical, co-rotating template.

In particular, a homogeneous bend of circular arc shape can be imposed on the sample over an extended region. This leads to a homogenous state of stress in this region.

Another preferred embodiment is characterized in that, at least in the margin region of the sample that has been bent in a circular arc shape, the bending radius R imposed on the section of the sample to be examined lies in an interval between a lower value $R_{min}$ and an upper value $R_{max}$, so that $R_{min} \leq R \leq R_{max}$, where $R_{min} = E*t/(2*\sigma*(1-f))$ and $R_{max} = E*t/(2*\sigma*(1+f))$ and where E stands for the modulus of elasticity of the sample material, σ stands for a predetermined tensile stress, and f is a number between 0 and 1, in particular 0.5, preferably 0.25, more preferably 0.1.

In this embodiment, a relation is created between the bending radius R of the sample and the tensile stress σ acting on its margin. This makes it possible to adjust the desired test tensile stress σ through the choice of the corresponding bending radius or vice versa. This is based on the following relation:

The exact bending stress σ at the margin of a sample with thickness t and modulus of elasticity E is described to good approximation by the equation $$\sigma = E*t/(2*R). \tag{1}$$

Here, R is the bending radius of the sample in the neutral plane of the sample. The latter typically corresponds to the middle plane between lateral faces of the sample.

In accordance with the invention, thin samples, in particular, are examined, so that the difference between the bending radius R of the neutral plane and the bending radii of the lateral faces is generally negligible.

Also preferred is a method according to the invention that is characterized in that the template surface is designed as a cylinder or as a cylinder sector having a constant radius $R_L$, so that the template surface has a cross section of circular arc shape with a constant radius $R_L$, or is designed as a cone or as a cone sector, so that the template surface at least at one point has a cross section of circular arc shape with a constant radius $R_L$, and wherein this template surface of circular arc shape in cross section is concave, and for the sample in the section of the sample to be examined the bend of circular arc shape with the radius R is imposed on the margin of the sample to be examined, by pressing at least one section of the first lateral face of the sample flatly and radially against this concave template surface by a pressing force, so that this pressed section of the first lateral face of the sample is in flat contact with the concave template surface, or this template surface of circular arc shape in cross section is convex, and for the sample in the section of the sample to be examined, the bend of circular arc shape with the radius R is imposed on the margin of the sample to be examined by pressing at least one region of the second lateral face of the sample flatly and radially against this convex template surface by a pressing force from outside, so that this pressed section of the second lateral face of the sample is in flat contact with the convex template surface.

This embodiment is especially advantageous, because the use of the types of templates provided for here is especially simple and tolerant of error. The flat pressing against the respective template surface enables a homogeneous bending of the sample in a circular arc shape to be achieved. In this way, it is ensured that each point on the margin of the sample is subjected to the predetermined bending and is thereby subjected to the intended tensile stress.

The intention is to impose a bend having a radius R on the neutral plane of the sample. This can be achieved in an exact manner by using a concave template surface with a radius of curvature $R_L$, which corresponds to the desired radius R of the neutral plane of the sample in addition to the distance of this plane from the concave template surface in the pressed state of the sample. The same applies analogously for the use of a convex template, where, in this case, the radius $R_L$ of the template would be reduced with respect to R, corresponding to the distance of the neutral plane of the sample from the convex template surface. Therefore, $R_L=R+t/2$ would generally hold for a concave template surface or $R_L=R-t/2$ for a convex template surface. Both of these relations ensue from the fact that the neutral plane generally represents the middle plane of the sample, but a respective lateral face is pressed against the template surface. However, the difference between $R_L$ and R can be neglected in many cases and $R_L=R$ can be used.

Another embodiment is characterized in that in the section of the sample to be examined, the bend of circular arc shape with the bending radius R is imposed section by section on the margin to be examined along the margin to be examined, by moving the sample along the margin to be examined continuously or stepwise relative to the template.

This embodiment makes it possible to test margins of nearly any desired length. The relative movement between the margin and the template can induce a sliding of the margin on the template. However, this sliding can be prevented, for example, by rolling on a cylindrical, co-rotating template.

Another method according to the invention is characterized in that the template surface of the template is convex and the second lateral face of the sample is pressed against this convex template surface by the pressing force and the pressing force is transmitted onto the first lateral face of the sample or onto the second lateral face of the sample by a bendable band, wherein this bendable band preferably runs parallel to the margin of the sample to be examined and is preferably distanced from the margin to be examined and is preferably attached adhesively to the first lateral face or the second lateral face of the sample and preferably protrudes above the sample and this bendable band is preferably designed to be flexible and this bendable band is preferably designed to be self-adhering.

The bendable band enables the sample to be pressed reliably against the template. This embodiment, which is characterized as being preferred, substantially facilitates handling of the sample.

Another embodiment of the method is characterized in that the template surface is convex and comprises the following steps: adhesive attachment of a bendable band to the first lateral face of the sample or the second lateral face of the sample parallel to the margin to be examined and distanced from the margin of the sample to be examined, wherein this bendable band is preferably designed to be self-adhering and this bendable band is preferably designed to be flexible; placing the sample on the convex template surface, so that the second lateral face of the sample is in contact with the convex template surface; adjustment of the balance of forces acting on the sample particularly by means of the bendable band, so that the sample, in the section to be examined is bent over the convex template surface and the second lateral face of the sample is flatly pressed against the convex template surface, so that the second lateral face of the sample assumes at least temporarily a bend of circular arc shape with the bending radius $R_L$ of the template surface at the margin to be examined, and preferably displacement of the sample relative to the template along the margin to be examined, so that the section of the sample that has been subjected to the bending radius $R_L$ of the template surface is increased along the margin to be examined and this examined section of the margin of the sample extends over the margin to be examined.

This embodiment has the advantage that the adhesively attached bendable band can hold together the shards if the sample breaks. This is expeditious in regard to a conceivable further analysis of the broken sample. Moreover, if the method is carried out manually, the work safety is thereby increased. In this case, the bendable band can also serve as a kind of "handle" for the sample, by means of which an operator grasps the sample and, if need be, bends it over the template by exerting tensile forces. However, the balance of forces acting on the sample can also be adjusted without pulling the band in the direction of the template, because thin samples, in particular, can be wrapped around a template in many template geometries solely under the influence of their own weight.

Another embodiment of the method is characterized in that an elongated sample is used, in which the margin to be examined forms a lengthwise edge.

This is especially advantageous in the case when fractures that seldom occur per unit length of the sample margin are to be investigated, as well as for extended samples.

Also in accordance with the invention is a method in which an examination of the fracture strength of the margin of samples to be examined is performed on both sides, by examining the fracture strength of the first lateral face at the margin to be examined, as described, and then examining the fracture strength of the second lateral face at the margin to be examined, as described, wherein—preferably—the first lateral face at the margin of the sample to be examined is examined by means of the template and the sample is rotated or the template is rotated and/or displaced, so that the first lateral face and the second lateral face of the sample are exchanged relative to the template surface of the template, and then the second lateral face of the sample is examined at the margin to be examined by means of the template.

The fracture probabilities of glass samples, in particular, can depend on the direction of bending. It can depend on which lateral face is bent outward and which lateral face is bent inward during bending. The last-mentioned embodiment enables a sample to be examined regardless of this effect.

The method according to the invention enables the tensile stress at break $\sigma_b$ of the sample to be determined. Said tensile stress at break must lie, at the conclusion of the method, between the highest stress that the sample has withstood and the stress that corresponds to the predetermined bending radius at which the sample has fractured. The bending radii R can be achieved, for example, by using a plurality of templates having different template radii $R_L$. If the sample has already fractured during bending with the largest radius R, then its tensile stress at break $\sigma_b$ lies below the range of measurement; if it has not fractured at the smallest bending radius R, then its tensile stress at break $\sigma_b$ lies above the range of measurement.

An apparatus according to the invention for testing the fracture strength of flat samples made of brittle-fracture material, in particular of glass sheets, having a first lateral face and a second lateral face as well as at least one margin, wherein the second lateral face lies opposite to the first lateral face and the margin forms a transition from the first lateral face to the second lateral face and the sample has a thickness t at this margin, in regard to fractures originating under a mechanical tensile stress σ at this margin to be examined, in particular by means of a method described in this application, comprises a bending device for imposing a homogeneous, convex bend of circular arc shape on the sample with a predetermined bending radius R in the region of the margin to be examined along this margin, wherein this bending device comprises: a template for predetermining the bend of circular arc shape, having a template surface for pressing of the sample, wherein this template surface is designed as a cylinder or cylinder sector or as a cone or cone sector, so that the template surface has a cross section of circular arc shape and is designed to be dimensionally stable, as well as a pressing device for flat pressing of the first lateral face or of the second lateral face of the sample against the template surface by exerting a pressing force directed radially to the template.

Moreover, another apparatus according to the invention comprises a feeding device for advancing the sample along the margin to be examined of the sample relative to the template.

This embodiment makes it possible to examine samples in an automated manner.

A multiple template according to the invention for determining the mechanical tensile stress at break $\sigma_b$ of flat samples made of brittle-fracture material, in particular of glass sheets, having a first lateral face and a second lateral face as well as at least one margin, wherein the second lateral face lies opposite to the first lateral face and the margin forms a transition of the first lateral face to the second lateral face and the sample has a thickness t at this margin, in regard to fractures originating from this margin to be examined, in particular by means of the above-described method for determining the mechanical tensile stress at break of flat samples, in a range from a minimum tensile stress at break $\sigma_{min}$, which is to be determined, up to a maximum tensile stress at break $\sigma_{max}$, which is to be determined, comprises at least four, preferably at least five, templates for examining the fracture strength of samples, wherein these templates each have a template surface that is designed to be dimensionally stable and is designed as a convex cylinder or cylinder sector, and wherein these cylindrical templates each have a radius $R_i$, where i is a number between 0 and (N−1) and where N is the number of templates of the multiple template, and wherein these template radii $R_i$ differ between the templates, and the following relation applies:

$$R_{i+1} < R_i \text{ for } i=0 \text{ to } i=(N-2), \text{ and}$$

$$R_{i,min} < R_i < R_{i,max},$$

where $$R_{i,min} = R_{i,q} * (p*q)^{\wedge(-1/2)} \text{ and}$$

$$R_{i,max} = R_{i,q} * (p*q)^{\wedge(+1/2)},$$

and where $R_{i,q} = R_0 * q^{\wedge(-i)}$ corresponds to a geometric series with a "multiplication factor" q and wherein this "multiplication factor" is $$q = (\sigma_{max}/\sigma_{min})^{\wedge(1/N-1))} = (R_{N-1}/R_0)^{\wedge(-1/N-1))} \text{ and}$$

p is a real number between 0 and 1, where preferably p<0.99, more preferably p<0.5, most preferably p<0.01.

This multiple template is suitable especially for determining the tensile stress at break $\sigma_b$ of samples, because, correspondingly stepped, it makes available the required templates and bending radii.

Another multiple template according to the invention for examining the fracture strength of a plurality of flat samples made of brittle-fracture material, in particular of glass sheets, in which the samples each have a first lateral face and a second lateral face as well as at least one margin and the first lateral face lies opposite the second lateral face and the margin forms a transition from the first lateral face to the second lateral face and the samples have different thicknesses $t_i$ (i=1, 2, 3 . . . ) at this margin, in regard to each of the fractures originating under a mechanical tensile stress σ from the margin to be examined of the respective sample, in particular according to one of the described methods or as a part of one the described apparatuses, comprises a plurality of templates for examining the fracture strength of flat samples with thicknesses $t_i$, where i a whole number between 1 and N, and where N is the number of templates comprised by the multiple template, and wherein these templates each have a dimensionally stable template surface for flat pressing of samples, and wherein these template surfaces are each designed as a convex cylinder or cylinder sector having a radius $R_i$, wherein the following relation applies to these radii: $R_{i+1} < R_i$ for 0<i<N−1, and the multiple template comprises at least three, preferably at least four, templates, wherein the radii $R_i$ of these at least three, preferably at least four, templates are different and each of them deviates by no more than 30%, preferably no more than 15%, more preferably by no more than 5%, from reference values, wherein these reference values are chosen from the set {C*20 μm, C*25 μm, C*30 μm, C*50 μm, C*70 μm, C*100 μm, C*145 μm, C*200 μm}, where C is a constant and preferably C=E/(2*σ), where E is the modulus of elasticity of the sample material (10), and σ is the tensile stress under which the samples (10) are to be examined.

This multiple template makes it possible to examine glass samples of different thickness t for their fracture strength under the same tensile stress σ.

A preferred embodiment of this multiple template is characterized in that the templates are arranged in such a way that the cylinder axes thereof are arranged parallel to one another in a plane and the individual template surfaces are arranged axially offset along the cylinder axes, and the cylindrically bent template surfaces are arranged concentrically or the template surfaces are arranged in such a way that their projections contact at one point in a plane perpendicular to the cylinder axes.

These arrangements of templates are space-saving and simplify the use of the templates, in particular the exchange between templates having various radii. These geometric arrangements of the individual templates are especially appropriate in operation.

The invention will be explained in detail below on the basis of exemplary embodiments with reference to the attached figures. In the figures, identical reference numbers refer to identical or corresponding elements.

BRIEF DESCRIPTION OF THE FIGURES

FIG. 5 is a flow chart of a method for determining the tensile stress at break of a sample.

DETAILED DESCRIPTION

Figure 1:
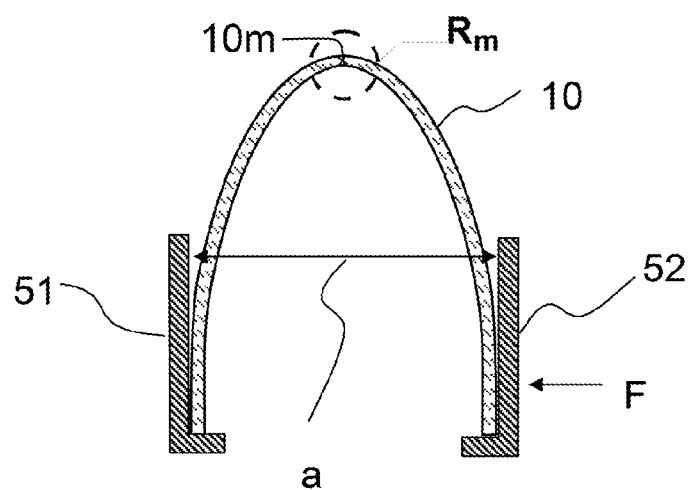
FIG. 1 is a schematic illustration of an apparatus for carrying out the hitherto used two-point bending method.

FIG. 1 shows a measurement arrangement for carrying out the known two-point bending method. In this method, thin glass samples 10 are clamped between two support plates 51, 52 and then bent by bringing these plates 51, 52 together.

In this case, an inhomogeneous state of stress, which is greatest in the middle 10m of the sample 10, is created. Accordingly, the bending radius of the sample 10 is also the smallest in the middle 10m between the two support plates 51, 52.

The tensile stress at break can then be determined by determining the minimum bending radius $R_m$ existing at fracture and by determining, on the basis of this value, the corresponding tensile stress at the edge. The tensile stress σ is hereby inversely proportional to the bending radius. The bending radius $R_{min}$, in turn, depends on the distance a between the two support plates 51, 52. In order to determine the tensile stress at break of the sample 10, the distance a between the two support plates 51, 52 can be recorded at the time point of fracture. Such an arrangement has the disadvantages already discussed above.

Figure 2A:
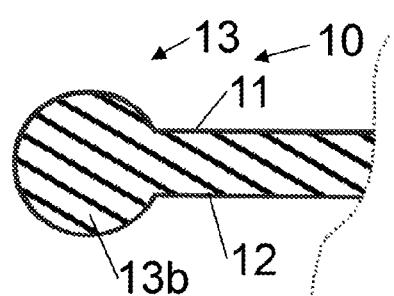
FIG. 2*a-c* is a schematic cross section of the margins of exemplary thin glass samples.

Shown schematically in FIG. 2a is the cross section of a sample margin 13. The thin glass sample 10 has the first lateral face 11 and the second lateral face 12. Here, the margin 13 of the sample 10 has the border 13b. The sample 10 is extended further out of the plane of the drawing.

Figure 2C:
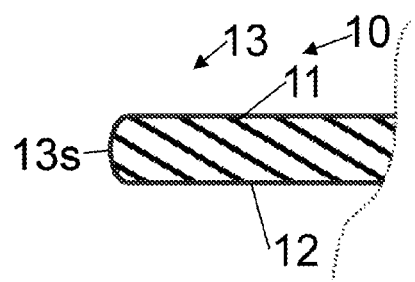
Figure 2B:
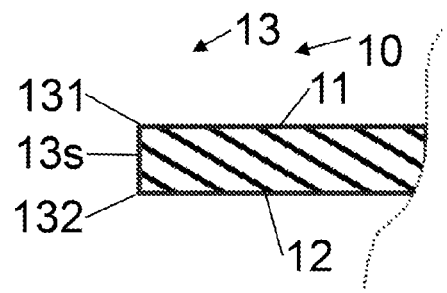

FIG. 2b shows, in analogy to FIG. 2a, another exemplary sample margin 13. This comprises the end face 13s as well as, at the transition of the first lateral face 11 to the end face 13s, the first corner 131 and, at the transition of the second lateral face 12 to the end face 13s, the second corner 132.

The sample margin 13 illustrated in FIG. 2c has the rounded end face 13s instead of the corners 131 and 132.

It is conventional among persons skilled in the art usually to refer to the regions of samples 10 named here as "margins" 13 also as "edges." This applies regardless of whether they have corners 131, 132 or, for example, are rounded.

An exemplary embodiment of the method according to the invention will be discussed below on the basis of FIGS. 3a to 3d. The examining of the margin strength of an exemplary brittle-fracture sample 10 having the thickness t under the mechanical tensile stress σ will be discussed. The material of the sample has a modulus of elasticity E. The following relation exists at the margin 13p of the sample 10—as already described in Equation (1)—between the mentioned quantities:

$$\sigma = E^*t/(2^*R).$$

In this equation, R is the bending radius of the sample 10 in the "neutral plane" 10n, that is, in the stress-free plane 10n in the middle of the sample, in which any tensile stress and compressive stress are eliminated. Given the predetermined bending radius R, the tensile stress σ corresponding to it is determined by means of this relation and, given the predetermined tensile stress σ the bending radius R to be imposed on the sample 10 corresponding to it is determined.

Figure 3A:
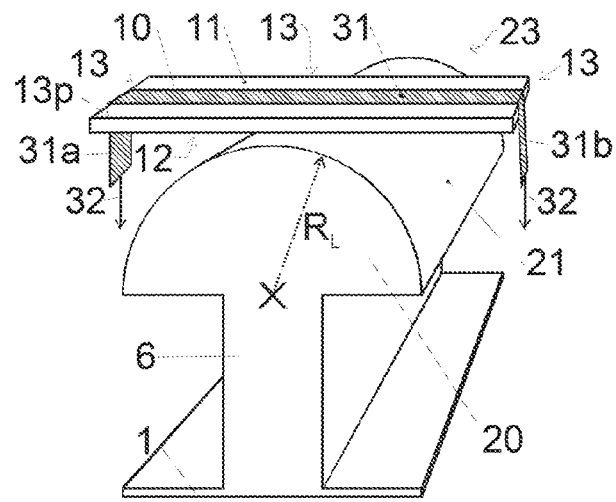
FIG. 3*a-c* is an illustration of a margin examination by means of a template designed as a cylinder sector.

FIG. 3a shows a perspective illustration of said exemplary thin glass sample 10 in the bending apparatus 23 prior to bending. The bending device 23 comprises the template 20 as well as the bendable band 31.

The template 20 has a cylindrical design; its surface 21 has the constant bending radius $R_L$, symbolized here by the arrow originating from the center point of this curve, which is marked as a cross. It is dimensionally stable in such a way that it is not deformed under the action of pressure. The template 20 shown here is made of metal. It is supported on the frame 6.

The rectangular sample 10 is made of thin glass having the thickness t. It has the four margins 13. The front margin 13p is to be examined for its fracture strength. The thickness t of the sample is typically between 5 µm and 500 µm.

The adhesive band 31 is adhered to the first lateral face 11 of the sample. It runs at a certain distance from the margin 13p to be examined and is essentially parallel to the latter. It has been found that this band 31 should be both bendable and flexible and/or stretchable. Various commercially available types of adhesive bands made of thin plastic have proven well suited for this purpose. The adhesive band 31 has a number of functions. On the one hand, the protruding ends 31a and 31b serve the operator as a convenient possibility for grasping the sample manually, laying it on the surface 21 of the template 20, and bending it over the template 20 by pulling in the direction of the arrow 32. On the other hand, the adhesive band 31 ensures that, when the sample 10 breaks, the shards remain adhered to this band 31. The shards of the sample 10 ideally remain adhered to the adhesive band 31 as a unit. This is advantageous, on the one hand, for preventing work accidents. On the other hand, it enables the fractured sample 10 or its shards to be analyzed without having to collect them beforehand and reassemble them similarly to a puzzle. It has been found that, within the framework of measurement accuracy, the adhesive band 31 has no influence on the result of the test.

If this function of the adhesive band 31 can be dispensed with as an element for holding together the shards, then, instead of the adhesive band 31, it is also possible to attach simple retaining pieces 31a and 31b to the short margins or edges of the sample without a continuous band 31 connecting them. If need be, the sample can also be grasped directly or can be clamped in other retaining devices.

Tests have shown that there are no special requirements placed on the geometry of the sample 10. The margin 13p to be examined should be straight, so that the adhesive strips 31 can readily be applied (a few mm behind the edge 13), so as then to pull or lay the sample 10 over the template 20. The length of the sample 10 is limited in practice only by handling. Ultimately, long samples 10 have to be drawn over the template 20 and thus the practical limit of the sample length is approximately 600 to 800 mm. Nor is there any fundamental limitation in the width of the sample 10. If the sample 10 is too wide, it can "droop" in back when it is put in place/pulled, which strongly impairs the measurement in the absence of any countermeasures. It cannot be ruled out that wide samples 10 will also lead at the margin to be examined 13 (measurement edge) to additional stresses that will not be taken into consideration in a simple analysis. It is therefore advantageous when the samples 10 are not wider than 100 mm. Preferably, the ratio of length to width is not less than 1.

Figure 3B:
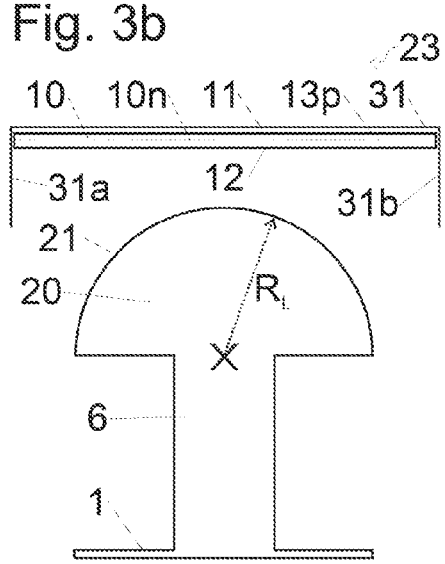

FIG. 3b shows the content of FIG. 3a in a projection in crosswise direction. The adhesive band 31 is illustrated at a distance from the first lateral face 11 only for purpose of illustration; in reality, it is attached adhesively to it. The dotted line 10n marks the middle plane 10n of the sample 10.

Figure 3C:
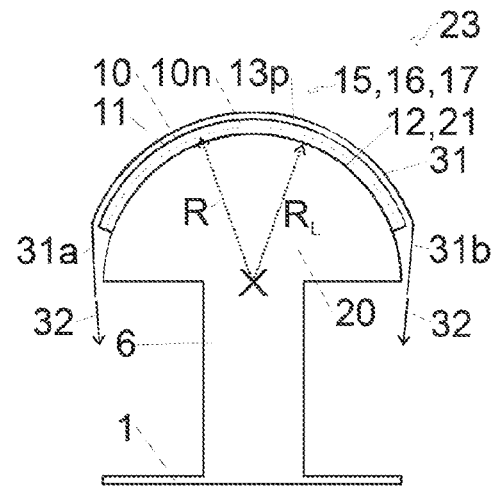

The subject of FIG. 3c corresponds to that of FIG. 3b. However, tensile forces 32 are now exerted on the ends 31a and 31b of the adhesive band 31 in the direction of the template 20. As a result, the second lateral face 12 of the sample 10 is pressed against the cylindrical surface 21 of the template 20. The sample 10 is bent, so that the second lateral face 12 of the sample 10 rests flatly against the template surface 21. The second lateral face 12 of the sample 10 assumes the bending radius $R_L$ of the template surface 21. Relevant for the tensile stress σ acting on the sample margin 13p is the bending radius R of the "neutral plane" 10n of the sample 10. When regarded exactly, this is thicker than $R_L$ by half a sample thickness, that is, t/2 greater. However, this can be neglected and R=$R_L$ can be assumed for simplicity. In the context of this approximation, the bend 16 of the template surface 21 is thus imposed on the sample 10; the sample margin 13p is subjected to the corresponding tensile stress σ in the region of the first lateral face 11 to good approximation.

In another exemplary embodiment, the adhesive band 31 is adhered onto the second lateral face 12 of the sample 10. If the adhesive band 31 is sufficiently thin, there is no significant change in the bending radius R of the sample 10. This arrangement has the advantage that any influence of the adhesive band 31 on the first lateral face 11 of the sample 10 is thereby excluded. Moreover, the adhesive band 31 can protect the second lateral face 12 at least partially from being scratched on the template surface 21.

Figure 4A:
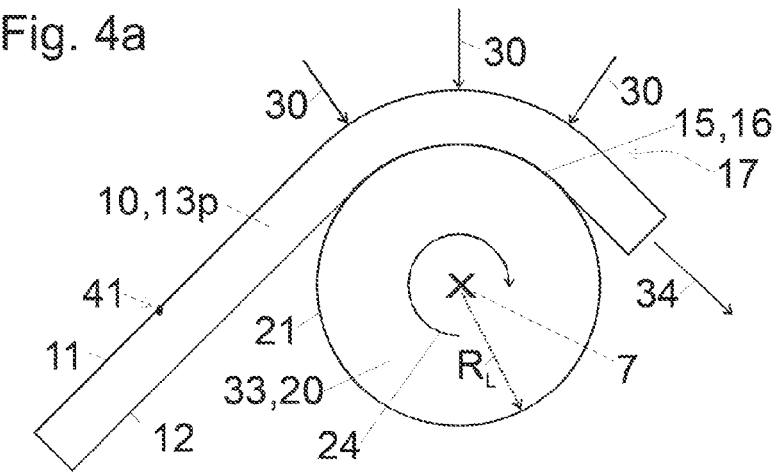
FIG. 4a-c are illustrations of a margin examination by means of a rotating, cylindrical template.
Figure 4B:
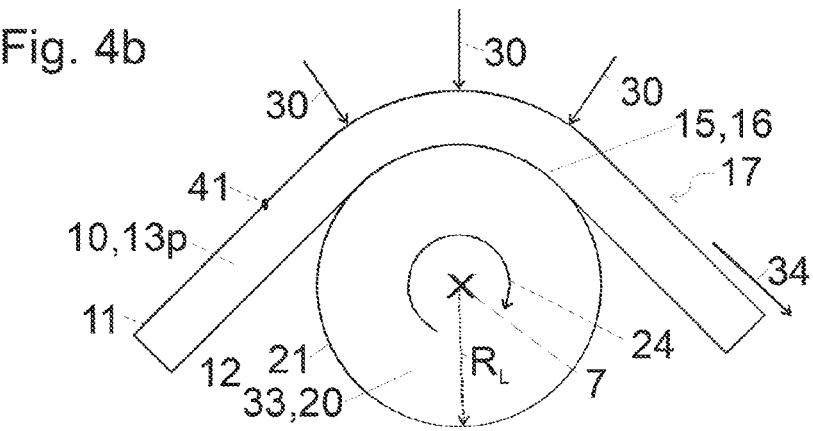
Figure 4C:
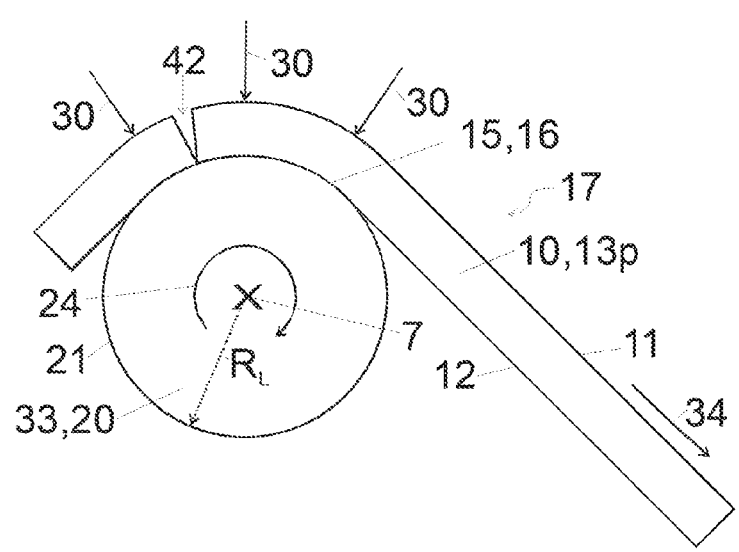

To be discussed on the basis of FIGS. 4a to 4c is another exemplary embodiment that is explained on the above constructed exemplary embodiment. Once again, the margin 13p of the sample 10 is examined for fracture strength. The template 20 is now designed as a rotatable solid cylinder 20. The sample 10 has a defect 41 at the margin 13p in the region of its first surface 11.

In this example, moreover, the sample 10 is longer along the margin 13p to be examined than in the preceding example. In this case, only a section 15 of the margin 13p of the sample is pressed against the template at a given time. The bend of circular arc shape 16 of the template surface 21 is further imposed on this section 15 of the sample 10. In this section 15, the sample 10 has just been examined at the respective point in time; outside of this section 15, however, the sample 10 is no longer in contact with the template surface 21.

As shown in FIG. 4a, the sample 10 is placed with its second lateral face 12 on the cylindrical surface 21 of the template 20. It is pressed by pressing forces 30, which are directed radially to the cylindrical template 20 or normal to the template surface 21, in the section 15 against the template 20. This occurs in such a way that the sample 10 bends over the template 20 and the second lateral face 12 of the sample 10 or of the sample margin 13p and assumes the bend of the template 20 having bending radius $R_L$ in the pressed section 15 as long as this section 15 is pressed. Once again, it may be assumed that the bending radius R of the neutral plane 10n (not drawn in here) corresponds to that of the template 20 to good approximation.

The sample 10 is transported further in the feeding direction 34 with continued pressing 30, with the axis 7 of the template 20 remaining fixed in position and the template 20 rotating in the direction of rotation 24 shown, so that the second lateral face 12 of the sample 10 does not slide over the template surface 21, but rather rolls. This makes it less likely that the test itself could lead to further surface defects, which could potentially falsify the result.

In FIG. 4b, the sample has been transported further. The section 17 of the sample, which has been subjected to the bend 16 having the bending radius R, leaves the template 20 in the direction 34 and continues to emerge. The exemplary defect 41 comes closer to the bending template 20.

In FIG. 4c, the already bent and thereby examined section 17 has increased further. Moreover, the defect 41 has migrated into the presently bent section 15. There, under the tensile stress σ, it has led to the formation of the crack 42. The sample 10 breaks.

The cylindrical template 20 can be actively rotated and thus act simultaneously as a feeding device 33 for the sample 10. However, it can also merely co-rotate, while an operator pulls the sample 10 manually over the template 20.

In another exemplary embodiment, the template 20 is not rotatably mounted. Instead, the sample 10 is pulled in a sliding manner over the template surface 21. In this case, the template 20 need not be a solid cylinder as well; a template surface 21, which, as illustrated schematically in FIGS. 3a to 3c, forms a partial cylinder 21 or a cylinder sector 21, is sufficient in this case.

Figure 4D:
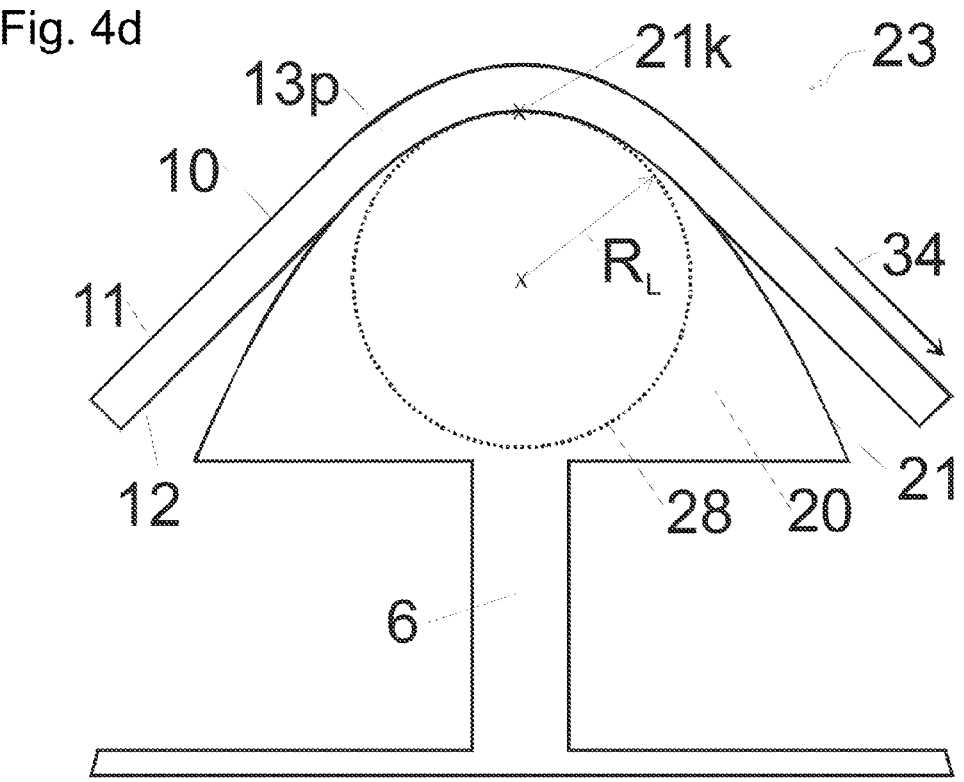
FIG. 4d is an illustration of a margin examination by means of a template designed as a parabola.

In FIG. 4d, a template 20 is illustrated in an analogous manner to FIG. 4a-c and FIG. 3a-c. In this case, however, the template surface 21 is not cylindrical, but rather parabolic in design. At the apex 21k, this parabola 21 has a local curvature with a radius of curvature $R_L$; the corresponding radius of curvature 28 of the template surface 21 at this point is indicated by a dashed line. In this embodiment, each point of the margin of the sample 10 is subjected to a bending 21k corresponding to this curvature 21k in that the sample 10 is transported in the pressed state in the direction of the arrow 35. Such a shape of the template, which does not have a cylindrically arched template surface, is also suitable for testing whether a sample 10 is able to withstand an increased bending stress. If, however, a sample 10 is stressed until it breaks, there exists the drawback that only the site of fracture would need to be localized in order to establish the stress at which the sample has fractured, since the fracture does not necessarily occur at the apex with the minimum radius of curvature $R_L$. Cylindrically arched template surfaces, by contrast, impose a constant curvature on the sample, so that the tensile stress at break can be determined independently of the site of fracture.

It is obvious that a diversity of other template shapes 20 can be formed without departing from the scope of the invention. What is important is that, at least initially, a defined curvature 21k is imposed on the sample 10 by the template surface 21. This local curvature 21k can then be shifted over the sample 10 by a relative displacement between the sample 10 and the template surface 21 along the margin 13p, so that a region 13p of the sample 10 to be defined by this displacement has been subjected to a bend 21k having the fixed minimum radius R.

FIG. 5 shows an exemplary embodiment of the method according to the invention for determining the tensile stress at break $\sigma_b$ of the sample 10. Initially, in the step 52, a template radius $R_L$ or a tensile stress $\sigma$ corresponding to it is predetermined and the sample 10 is subjected to these loads at its margin 13p to be examined—in particular, as described above—to a bend 16 by means of a corresponding template (step 53). Then, in step 54, it is examined whether the sample 10 has fractured starting at the margin 13p to be examined. Samples 10 that have not fractured starting from any margin or that have fractured starting from a margin 13 different from the margin 13p of interest are usually removed (not shown).

If the sample 10 has not fractured, the template radius $R_L$ is reduced or the predetermined tensile stress $\sigma$ is increased (step 55) and the sample 10 is once again subjected in step 53 to a bend 16, which now has the reduced bending radius $R_L$.

The steps 53, 54, and 55 are repeated until, in step 54, a fracture of the sample 10 is detected. If the sample 10 has fractured starting from the margin 13p to be examined, then the bending stress $\sigma_k$ corresponding to the last bending radius $R_L$ at which the sample did not fracture is recorded. The same holds true for the bending stress $\sigma_{k+1}$ that corresponds to the template bending radius $R_L$ at which the sample 10 has fractured. The tensile stress at break $\sigma_b$ lies in the interval $\sigma_k \leq \sigma_b \leq \sigma_{k+1}$. An appropriate approximation is the mean value of this interval.

If the sample 10 is fractured, it must be examined in any case whether this fracture originated from the margin 13p of interest or else from another point of the sample (for example, from a margin 13 that is not of interest or from the face area). This determination, in certain cases, can be carried out on the basis of a simple criterion: If a sample 10 fractures starting from a point 41 on its margin 13p, then a plurality of bundled cracks 42 originating from this point 41 often form. If such a bundle of cracks thus originates from the margin 13p of interest, then it is a fracture that needs to be detected. If a fracture 42 has not originated from the margin 13p of interest, then the corresponding stress value cannot be evaluated in the course of the observation of this margin 13p.

Figure 6A:
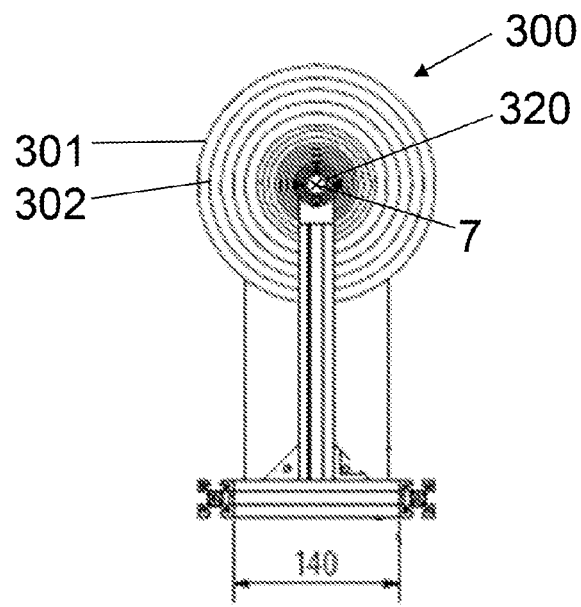
FIG. 6a is a cross-sectional projection of a concentric step roller.
Figure 6B:
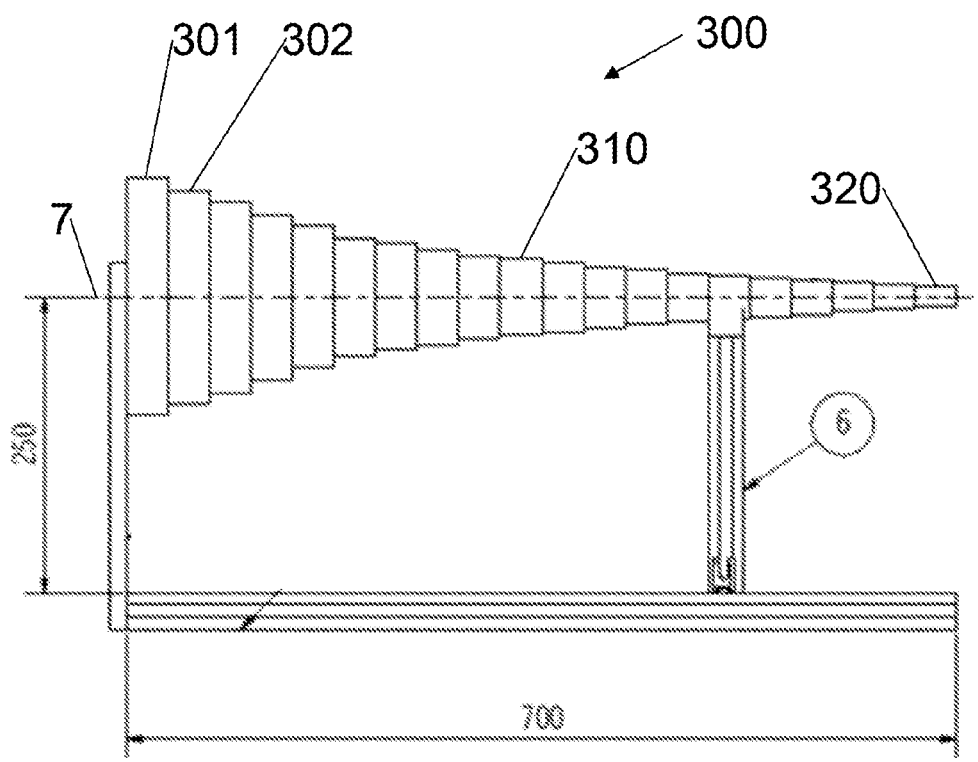
FIG. 6b is a longitudinal section of a concentric step roller.

In FIGS. 6a and 6b, a multiple template according to the invention is shown schematically in the form of a step roller 300, which is set up for determining the tensile stress at break $\sigma_b$ of samples 10 according to the method just discussed.

It is made up of a set 300 of discs 301 to 320, which are arranged concentrically. FIG. 6b shows the step roller 300 in longitudinal section and FIG. 6a shows a projection of the discs 301 to 320 in the crosswise direction. The discs 301 to 320 shown here were produced individually from plywood or plastic, in particular from POM, and are joined by the axis 7. However, they can also be rotated as a single workpiece, for example. It must only be possible to work the material mechanically in such a way that the discs 301 to 320 can be produced with sufficient accuracy, and the material must be strong enough that it does not deform when the glass samples 10 are placed on it and pulled over it. The discs 301 to 320 are held by the frame 6.

The discs 301 to 320 can be mounted rotatably or not rotatably. A rotatable mounting of the axis 7 and/or of the individual discs 301 to 320 has the advantage that, in this way, the sample 10 can be moved relative to the respective disc 301 to 320 with co-rotation of this disc 301 to 320. Thus, the second lateral face 12 of the sample 10, which is in contact with the surface 21 of the respective disc 301 to 320, does not need to slide over this surface 21; the risk of scratching the lateral face 12 of the sample 10 is thereby reduced.

If the tensile stress at break $\sigma_b$ of a sample 10 is to be determined, then this sample 10 is placed in succession on the discs 301 to 320 and pressed—for example, as discussed above on the basis of FIGS. 3a to 3c—until it breaks. In another exemplary embodiment, the samples are pulled over the discs 301 to 320 as explained above in conjunction with the method discussed on the basis of FIGS. 4a to 4c, for example.

In the exemplary realization of the exemplary embodiment here, the discs 301 to 320 have the following radii:

| Reference number of the disc | Plate radius $R_L$ [mm] |
|---|---|
| 301 | 300 |
| 302 | 275 |
| 303 | 250 |
| 304 | 230 |
| 305 | 210 |
| 306 | 192 |
| 307 | 175 |
| 308 | 160 |
| 309 | 147 |
| 310 | 134 |
| 311 | 122 |
| 312 | 112 |
| 313 | 103 |
| 314 | 94 |
| 315 | 86 |
| 316 | 78 |
| 317 | 71 |
| 318 | 65 |
| 319 | 60 |
| 320 | 55 |

In choosing these radii $R_L$, attention was paid to keeping the ratio of adjacent radii $R_i$ and $R_{i+1}$ approximately constant. A constant ratio of the radii $q := R_i/R_{i+1}$ (with a deviation of preferably $\Delta q < 1\%$) according to Equation (1), in the case of equivalent samples, leads to a mutually reciprocal, likewise constant ratio of the corresponding bending stresses $\sigma_{i+1}/\sigma_i = q$. This geometric gradation of the stresses or radii is especially advantageous for the characterization of ensembles of samples 10, because the fracture of glass samples 10 under a tensile stress $\sigma$ at the margin 13p is a statistical effect. As a result of the gradation with constant ratio of the radii or stress ratio q, the relevant values of the distribution function can be read from the distribution of the measured values for $\sigma_b$ without further transformation.

In the following table, further advantageous gradations of radii and the tensile stresses $\sigma$ corresponding to them are listed in units of Megapascals (MPa) for the glasses D 263 (with the modulus of elasticity E=72.9 GPa) and AF 32 (E=74.8 GPa) for glass thicknesses of t=0.05 mm (both types of glass) as well as t=0.1 mm and t=0.2 mm (only AF 32).

| | | Tensile stress $\sigma$ [MPa] | | | |
|---|---|---|---|---|---|
| i | $R_i$ [mm] | D 263 t = 0.05 mm | AF 32 t = 0.05 mm | AF 32 t = 0.1 mm | AF 32 t = 0.2 mm |
| 1 | 100 | 18.2 | 18.7 | 37.4 | 74.8 |
| 2 | 91.74 | 19.9 | 20.4 | 40.8 | 81.5 |
| 3 | 84.17 | 21.7 | 22.2 | 44.4 | 88.9 |
| 4 | 77.22 | 23.6 | 24.2 | 48.4 | 96.9 |
| 5 | 70.84 | 25.7 | 26.4 | 52.8 | 105.6 |

-continued

| | | Tensile stress σ [MPa] | | | |
|---|---|---|---|---|---|
| i | $R_i$ [mm] | D 263 t = 0.05 mm | AF 32 t = 0.05 mm | AF 32 t = 0.1 mm | AF 32 t = 0.2 mm |
| 6 | 64.99 | 28 | 28.8 | 57.5 | 115.1 |
| 7 | 59.63 | 30.6 | 31.4 | 62.7 | 125.4 |
| 8 | 54.7 | 33.3 | 34.2 | 68.4 | 136.7 |
| 9 | 50.19 | 36.3 | 37.3 | 74.5 | 149 |
| 10 | 46.04 | 39.6 | 40.6 | 81.2 | 162.5 |
| 11 | 42.24 | 43.1 | 44.3 | 88.5 | 177.1 |
| 12 | 38.75 | 47 | 48.3 | 96.5 | 193 |
| 13 | 35.55 | 51.3 | 52.6 | 105.2 | 210.4 |
| 14 | 32.62 | 55.9 | 57.3 | 114.7 | 229.3 |
| 15 | 29.92 | 60.9 | 62.5 | 125 | 250 |
| 16 | 27.45 | 66.4 | 68.1 | 136.2 | 272.5 |
| 17 | 25.19 | 72.4 | 74.2 | 148.5 | 297 |
| 18 | 23.11 | 78.9 | 80.9 | 161.9 | 323.7 |
| 19 | 21.2 | 86 | 88.2 | 176.4 | 352.8 |
| 20 | 19.45 | 93.7 | 96.1 | 192.3 | 384.6 |
| 21 | 17.84 | 102.1 | 104.8 | 209.6 | 419.2 |
| 22 | 16.37 | 111.3 | 114.2 | 228.5 | 456.9 |
| 23 | 15.02 | 121.4 | 124.5 | 249 | 498.1 |
| 24 | 13.78 | 132.3 | 135.7 | 271.4 | 542.9 |
| 25 | 12.34 | 144.2 | 147.9 | 295.9 | 591.7 |
| 26 | 11.6 | 157.2 | 161.3 | 322.5 | 645 |
| 27 | 10.64 | 171.3 | 175.8 | 351.5 | 703.1 |
| 28 | 9.76 | 186.7 | 191.6 | 383.2 | 766.3 |
| 29 | 8.95 | 203.5 | 208.8 | 417.7 | 835.3 |
| 30 | 8.22 | 221.8 | 227.6 | 455.2 | 910.5 |
| 31 | 7.54 | 241.8 | 248.1 | 496.2 | 992.4 |
| 32 | 6.91 | 263.6 | 270.4 | 540.9 | 1081.7 |
| 33 | 6.34 | 287.3 | 294.8 | 589.5 | 1179.1 |
| 34 | 5.82 | 313.1 | 321.3 | 642.6 | 1285.2 |
| 35 | 5.34 | 341.3 | 350.2 | 700.4 | 1400.9 |
| 36 | 4.9 | 372 | 381.7 | 763.5 | 1527 |
| 37 | 4.49 | 405.5 | 416.1 | 832.2 | 1664.4 |
| 38 | 4.12 | 442 | 453.5 | 907.1 | 1814.2 |
| 39 | 3.78 | 481.8 | 494.4 | 988.7 | 1977.5 |
| 40 | 3.47 | 525.2 | 538.9 | 1077.7 | 2155.4 |
| 41 | 3.18 | 572.4 | 587.4 | 1174.7 | 2349.4 |
| 42 | 2.92 | 624 | 640.2 | 1280.4 | 2560.9 |
| 43 | 2.68 | 680.1 | 697.8 | 1395.7 | 2791.4 |
| 44 | 2.46 | 741.3 | 760.6 | 1521.3 | 3042.6 |
| 45 | 2.26 | 808 | 829.1 | 1658.2 | 3316.4 |
| 46 | 2.07 | 880.8 | 903.7 | 1807.4 | 3614.9 |
| 47 | 1.9 | 960 | 985.1 | 1970.1 | 3940.2 |
| 48 | 1.74 | 1046.4 | 1073.7 | 2147.4 | 4294.8 |
| 49 | 1.6 | 1140.6 | 1170.3 | 2340.7 | 4681.4 |
| 50 | 1.47 | 1243.3 | 1275.7 | 2551.3 | 5102.7 |

Preferred, in particular, are sets of at least five discs having different radii, which are chosen from the above table.

The classification of the individual radii into a geometric sequence is illustrated once again below. A range of measurement of bending stresses with the upper limit $\sigma_{max}$ and the lower limit $\sigma_{min}$ is predetermined. This range is to be subdivided geometrically into N individual stresses $\sigma_n$. The maximum radius $R_1$ corresponds via Equation (1) to $\sigma_{min}$ and the minimum radius $R_N$ corresponds to $\sigma_{max}$. Regarded strictly mathematically (omitting the sample thickness), the "multiplication factor" for this series of radii would be:

$$q = \sigma_{i+1}/\sigma_i = (\sigma_{max}/\sigma_{min})^{(1/(N-1))} = (R_1/R_N)^{(1/(N-1))}.$$

This results in the following equation for the individual radii:

$$R_{i+1} = q*R_i = R_1*q^{(i-1)}.$$

It has been found that, in a range from $\sigma_{max}/\sigma_{min} \approx 1.5$ for four gradations, a multiplication factor of $q \approx (1.5)^{(1/5)}$ to $(1.5)^{(1/4)}$, that is, $q \approx 1.09$, affords experimentally reasonable results.

The calculated radii $R_i$ and gradations can be obtained roughly as follows. Appropriate is a real value $$R_{i,real} \in [R_{i,min}, R_{i,max}]$$

with $$R_{i,min} = R_i*(q^{(-1/2)}); R_{i,max} = R_i*(q^{(+1/2)}),$$

and further preferably $$R_{i,min} = R_i*(q*p)^{(-1/2)}; R_{i,max} = R_i*(q*p)^{(1/2)}$$

with the positive distance factor p<1, which is preferably 0.99, more preferably 0.5, and most preferably 0.01.

In the following table, exemplary radii $R_i$, including the lower and upper limits for p=1 and p=0.99, are given:

| | | p = 1 | | p = 0.99 | |
|---|---|---|---|---|---|
| i | $R_i$ [mm] | $R_{i,min}$ [mm] | $R_{i,max}$ [mm] | $R_{i,min}$ [mm] | $R_{i,max}$ [mm] |
| 1 | 100.00 | 95.8 | 104.4 | 96.3 | 103.9 |
| 2 | 91.74 | 87.9 | 95.8 | 88.3 | 95.3 |
| 3 | 84.17 | 80.6 | 87.9 | 81.0 | 87.4 |
| 4 | 77.22 | 74.0 | 80.6 | 74.3 | 80.2 |
| 5 | 70.84 | 67.9 | 74.0 | 68.2 | 73.6 |
| 6 | 64.99 | 62.3 | 67.9 | 62.6 | 67.5 |
| 7 | 59.63 | 57.1 | 62.3 | 57.4 | 61.9 |
| 8 | 54.70 | 52.4 | 57.1 | 52.7 | 56.8 |
| 9 | 50.19 | 48.1 | 52.4 | 48.3 | 52.1 |
| 10 | 46.04 | 44.1 | 48.1 | 44.3 | 47.8 |
| 11 | 42.24 | 40.5 | 44.1 | 40.7 | 43.9 |
| 12 | 38.75 | 37.1 | 40.5 | 37.3 | 40.3 |
| 13 | 35.55 | 34.1 | 37.1 | 34.2 | 36.9 |
| 14 | 32.62 | 31.2 | 34.1 | 31.4 | 33.9 |
| 15 | 29.92 | 28.7 | 31.2 | 28.8 | 31.1 |
| 16 | 27.45 | 26.3 | 28.7 | 26.4 | 28.5 |
| 17 | 25.19 | 24.1 | 26.3 | 24.2 | 26.2 |
| 18 | 23.11 | 22.1 | 24.1 | 22.2 | 24.0 |
| 19 | 21.20 | 20.3 | 22.1 | 20.4 | 22.0 |
| 20 | 19.45 | 18.6 | 20.3 | 18.7 | 20.2 |
| 21 | 17.84 | 17.1 | 18.6 | 17.2 | 18.5 |
| 22 | 16.37 | 15.7 | 17.1 | 15.8 | 17.0 |
| 23 | 15.02 | 14.4 | 15.7 | 14.5 | 15.6 |
| 24 | 13.78 | 13.2 | 14.4 | 13.3 | 14.3 |
| 25 | 12.64 | 12.1 | 13.2 | 12.2 | 13.1 |
| 26 | 11.60 | 11.1 | 12.1 | 11.2 | 12.0 |
| 27 | 10.64 | 10.2 | 11.1 | 10.2 | 11.1 |
| 28 | 9.76 | 9.3 | 10.2 | 9.4 | 10.1 |
| 29 | 8.95 | 8.6 | 9.3 | 8.6 | 9.3 |
| 30 | 8.22 | 7.9 | 8.6 | 7.9 | 8.5 |
| 31 | 7.54 | 7.2 | 7.9 | 7.3 | 7.8 |
| 32 | 6.91 | 6.6 | 7.2 | 6.7 | 7.2 |
| 33 | 6.34 | 6.1 | 6.6 | 6.1 | 6.6 |
| 34 | 5.82 | 5.6 | 6.1 | 5.6 | 6.0 |
| 35 | 5.34 | 5.1 | 5.6 | 5.1 | 5.5 |
| 36 | 4.90 | 4.7 | 5.1 | 4.7 | 5.1 |
| 37 | 4.49 | 4.3 | 4.7 | 4.3 | 4.7 |
| 38 | 4.12 | 3.9 | 4.3 | 4.0 | 4.3 |
| 39 | 3.78 | 3.6 | 3.9 | 3.6 | 3.9 |
| 40 | 3.47 | 3.3 | 3.6 | 3.3 | 3.6 |
| 41 | 3.18 | 3.0 | 3.3 | 3.1 | 3.3 |
| 42 | 2.92 | 2.8 | 3.0 | 2.8 | 3.0 |
| 43 | 2.68 | 2.6 | 2.8 | 2.6 | 2.8 |
| 44 | 2.46 | 2.4 | 2.6 | 2.4 | 2.6 |
| 45 | 2.26 | 2.2 | 2.4 | 2.2 | 2.3 |
| 46 | 2.07 | 2.0 | 2.2 | 2.0 | 2.1 |
| 47 | 1.90 | 1.8 | 2.0 | 1.8 | 2.0 |
| 48 | 1.74 | 1.7 | 1.8 | 1.7 | 1.8 |
| 49 | 1.60 | 1.5 | 1.7 | 1.5 | 1.7 |
| 50 | 1.47 | 1.4 | 1.5 | 1.4 | 1.5 |

Further preferred disc radii are: for sample glass thicknesses of t=0.03 mm and t=0.05 mm: $R_L$=39, 36, 33, 30, 27, 25, 23, 21, 19, 18, 16, 14, 12, 10, 8, 6, and 4 mm. For sample glass thicknesses of t=0.1 mm: $R_L$=71, 65, 60, 55, 50, 46, 42, 39, 36, 33, 30, 27, 25, 23, 21, 19, 18, 16, 14, 12, 10, 8, 6, 4 mm. For sample glass thicknesses of t for t=0.2 mm:

$R_L$=100, 92, 84, 77, 71, 65, 60, 55, 50, 46, 42, 39, 36, 33, 30, 27, 25, 23, 21, 19, 18, 16, 14, 12, 10 mm.

It is self-evident that the values and relations given as "radii" or "disc radii" in the present application are not limited to disc-shaped templates in the scope of the concrete exemplary embodiments, but rather are especially advantageous as bending radii also for use in the context of individual templates. The same holds true for (single or multiple) templates of any shape (for example, parabolic) with respect to the local radius of curvature at least at one point on the respective template surface 21 at the site 21k at which the sample 10 is to be pressed or is pressed against this surface 21.

Figure 7:
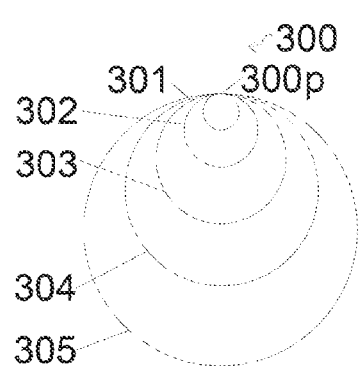
FIG. 7 is a cross-sectional projection of a non-concentric step roller.

Whereas, in the example shown in FIGS. 6a and 6b, the discs 301 to 320 are arranged concentrically with respect to one another, FIG. 7 shows an alternative arrangement to this. It shows a projection of the discs in the corresponding crosswise plane, so that the cylinder axes project out of the plane of the drawing. The discs 301 to 305 are arranged in such a way that the projections of their surfaces come into contact at a common point 300p. In the longitudinal direction (out of the plane of the drawing, not shown), the surfaces form a straight line, which connects the disc surfaces, at this point 300p. This embodiment has the advantage that, when a measurement is performed, it is easy to switch between various discs 301 to 305.

Another exemplary embodiment contains, instead of one or a plurality of discs 20 or 301 to 320, one or a plurality of templates 20, which has (have) a template surface 21 of circular arc shape 21 only in a narrow (angle) range and, moreover, can be shaped in any way. In other words, what are involved here are small sections taken from cylinder outer lateral surfaces and mounted on support stands. The respective sample 10 is pulled over these templates 20. This is of advantage, in particular, for very small bending radii R, because, in this case, the long samples 10 have to be pulled over the template 20 in any case and the fabrication of the templates 20 is thus simplified. However, in this case, it needs to be ensured that each point of the sample 10 has been subjected at least briefly to the corresponding bend 16. It has been found that it generally already suffices when, for this purpose, the sample 10 passes over a cylindrical sector 21 having a sector angle of 10° and the sample 10 is pressed flatly against the template 20 in this range 21. The reliability can be increased still further, if need be, by increasing the pressed angular region 21 up to at most 90°.

Furthermore, the multiple template can also be designed to be "stepless" in the form of a cone or truncated cone. In this case, the tensile stress at break $\sigma_b$ of samples 10 can be measured in a stepless manner in that the respective sample 10 is placed on a region of the template with a larger bending radius $R_L$ and moved under pressure on this multiple template to smaller bending radii $R_L$ until the sample 10 breaks. Viewed in this way, a cone or truncated cone can thus be regarded as a set of infinitely many, infinitesimally narrow templates 20.

The sample 10 can be pressed by means of the adhesive band 31 or another bendable band 31. However, it can also be pressed against the template 20 by means of a counterpiece ("die") that matches the template 20.

Moreover, instead of an outer cylinder 21, against which the second lateral face 12 of the sample 10 is pressed from the outside, it is also possible to use an inner cylinder (or a section of an inner cylinder). The first lateral face 11 of the sample 10 is pressed against it radially from the inside.

On the basis of fracture tests, it is also possible to carry out a method for the production of a glass article having at least one margin with a guaranteed fracture strength with respect to a specified mechanical tensile stress $\sigma_g$ at this margin, wherein a glass article is produced and the fracture strength of the margin of this glass article is tested under the specified tensile stress $\sigma_g$, preferably under 1.1 times the specified tensile stress $\sigma_g$, more preferably under 1.2 times the specified tensile stress $\sigma_g$, at least in a section of this margin, preferably at least along 0.01 times the length of this margin, more preferably at least along 0.1 times the length of this margin, in particular along the entire margin, by imposing a bend of the glass article on a template surface having a defined curvature, and the article is discarded provided that it breaks.

This method makes it possible to provide glass articles whose edge fracture strength has been examined.

A method for the manufacture of a thin, flat glass article can be further developed by examining the edge fracture strength with samples of such a glass article by means of one of the described methods and, on the basis of the edge fracture strength, determining a minimum bending radius $R_M$ and bending a glass article that is equivalent to the glass article from which the samples were obtained, with the bending radius $R_B$ not being less than the determined minimum bending radius $R_M$. In this case, the glass article from which the samples were obtained can also comprise the glass article to be examined. For example, the samples can be obtained by cutting off a section of the glass to be examined.

This method makes it possible on the basis of the samples to characterize and ensure the quality of glass articles that cannot be examined themselves.

Another method is characterized in that, as the glass article, a ribbon of glass is produced and wherein, after its production, the ribbon of glass is rolled up into a roll, with the bending radius $R_R$ of the ribbon of glass on the inner side of the roll not being less than the minimum bending radius $R_M$.

This method enables a rolled sheet of glass to be created without having to accept the existence of too many glass fractures.

Figure 8:
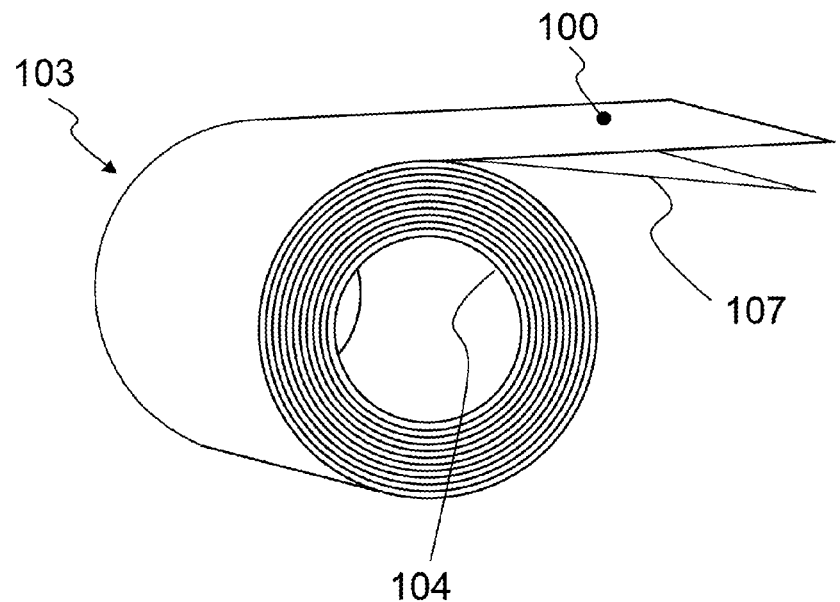
FIG. 8 is a roll of a ribbon of glass having a bending radius determined according to the invention.

Shown in FIG. 8 is a glass product 103 according to the invention. What is involved here is a rolled ribbon of glass 100. For this ribbon of glass, the minimum allowable bending radius was initially determined by means of the method according to the invention and the ribbon of glass was then rolled up. In the process, attention was paid to making the bending radius of the glass on the inner side 104 of the roll 103 larger than the allowable minimum bending radius. A sheeting material 107 (for example, paper or plastic) was rolled up into the roll with it in order to prevent the surfaces of the ribbon of glass from being scratched.

In order to be able to ensure an especially low rate of fracture even for very large-area glass articles, such as, in particular, thin ribbons of glass, it is also possible according to an embodiment of the invention to combine the method for examining the fracture strength of flat samples 10 with a bending test of a glass product 103. This embodiment of the invention is based on the idea that, by means of the method for examining the fracture strength of flat samples 10, initially one or a plurality of parameters relating to fracture strength, in particular one or a plurality of statistical parameters, are determined and, on the basis of these parameters, a bending radius for a bending test of the entire glass article is determined and the glass article is then subjected to the bending test, with the glass article being discarded if it breaks under the bending load at the fixed bending radius. It is appropriate to choose the bending radius of the glass article or the radius of curvature of the corresponding template surface of the template used to be greater than the mean value of the bending radius at which the samples 10 have broken.

In this way, the edges of glass articles, such as, in particular of glass sheets having defined radii, are bent and a bending stress is generated, which is sufficiently great so that the edges break at critical weak points, but, on the other hand, is sufficiently small that uncritical edge defects are not enhanced by the bending. In particular, it is to be ensured that the delivered glasses have warranted strength properties with adequate statistical reliability.

In order to design the bending radii for the bending test of the glass article, statistical strength tests are carried out on glass samples 10 in accordance with the method according to the invention, by means of which the "base strength" of the glass article is determined. The bending test should correspond to the range in which the strength properties of the glass article deviate in a negative way from those of random samples, that is, the fracture test according to the invention on glass samples with successively smaller bending radii.

According to an embodiment, by means of the method according to the invention for examining the fracture strength of flat samples 10, a random sample of N values is taken for the fracture bending radii $R_1 \ldots R_N$, and, for the values of these random samples, the mean value $$\langle R \rangle = \frac{1}{N} \sum_{i=1}^{N} R_i$$

and the variance $$s = \sqrt{\frac{1}{N-1} \sum_{i=1}^{N} (R_i - \langle R \rangle)^2}$$

are calculated.

Figure 9:
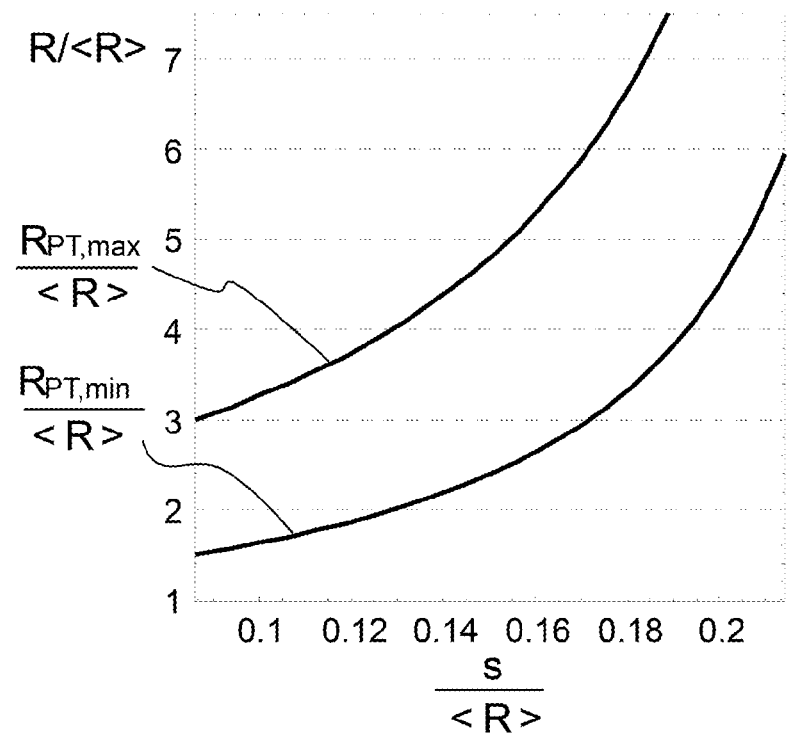
FIG. 9 to FIG. 11 illustrate maximum and minimum bending radii for a bending test of a glass article as a function of the statistical parameters obtained from fracture tests.

Then the entire glass article, in particular a ribbon of glass, is bent, preferably by feeding it over rollers, so that, depending on the relative variance $s/\langle R \rangle$, the bending radius $R_{PT}$ for the two bending directions lies in the range defined by the curves in FIG. 9, that is, between the two curves $R_{PT,max}$ and $R_{PT,min}$. In the diagram shown in FIG. 9, the ratio of the bending radius of the glass article to the mean value $\langle R \rangle$ of the bending radius when the samples 10 break is plotted on the ordinate as a function of the relative variance $s/\langle R \rangle$.

It is preferred that the number of random samples N is at least 20, that 10% of the largest values and 10% of the smallest values are discarded from the random samples, and that, from the rest (of the so-called "supported random samples"), only the mean value and the variance are derived according to the above two equations. The glass article is then subjected to a bending test by pulling it over rollers, for example, so that, depending on the relative variance $s/\langle R \rangle$, the bending radius $R_{PT}$ thereof lies in the region defined by the curves FIG. 10 for both bending directions.

The values $R_{PT,max}$ and $R_{PT,min}$ are functions of the relative variance $s/\langle R \rangle$. If the relative variance is high, this means that there is a large scatter of the bending stresses or, correspondingly, the bending radii in the fracture tests. Correspondingly, with higher scattering, larger bending radii are also chosen for the fracture test of the entire glass article in order to be able to ensure a specific fracture strength corresponding to the chosen bending radius.

Figure 10:
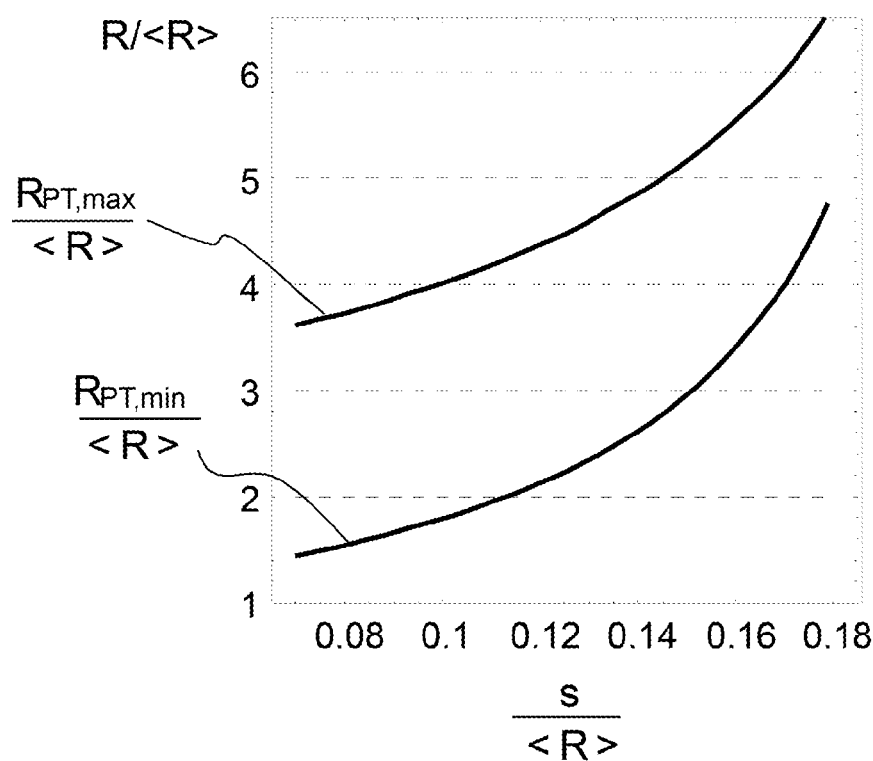

By choosing a bending radius between the curves $R_{PT,max}/\langle R \rangle (s/\langle R \rangle)$ and $R_{PT,min}/\langle R \rangle (s/\langle R \rangle)$ according to FIG. 9 or FIG. 10, which are oriented to the relative variance of the fracture strength of samples of an equivalent glass article and define a narrow region with a bending radius that is as small as possible, it is possible to ensure very high fracture strengths and still limit the rejects in the fracture test to glass articles that actually have significant weak points.

Figure 11:
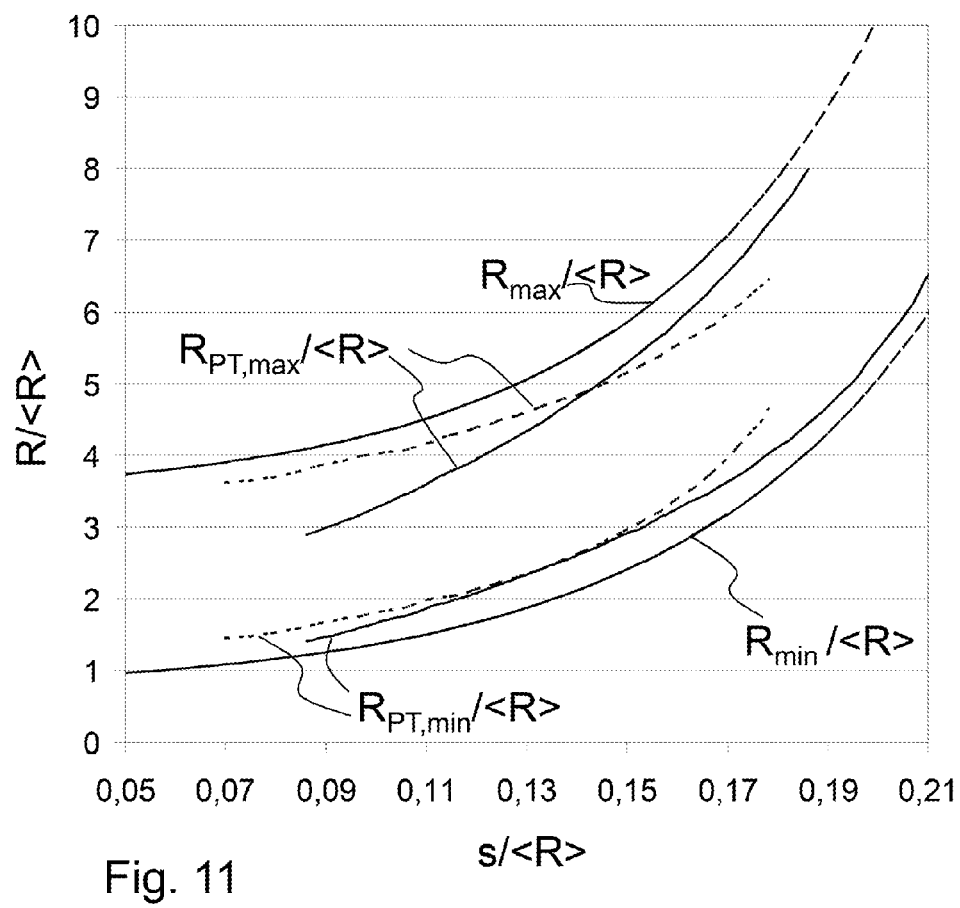

The regions between the curves $R_{PT,max}/\langle R \rangle$ and $R_{PT,min}/\langle R \rangle$ of FIG. 9 and FIG. 10 are slightly displaced against each other. For both of the test conditions mentioned above, namely, on the one hand, that of a random sample for which the values in the range of $R_{PT,max}/\langle R \rangle$ to $R_{PT,min}/\langle R \rangle$ according to FIG. 9 are favorable and, on the other hand, that of an adjusted random sample for which corresponding bending radii in the range of $R_{PT,max}/\langle R \rangle$ to $R_{PT,min}/\langle R \rangle$ result according to FIG. 10, it is possible to specify an enveloping region. For this purpose, FIG. 11 shows the curves $R_{PT,max}/\langle R \rangle$ and $R_{PT,min}/\langle R \rangle$ of FIGS. 9 and 10 as well as preferred limit values $R_{min}/\langle R \rangle (s/\langle R \rangle)$, $R_{max}\langle R \rangle (s/\langle R \rangle)$, between which the curves $R_{PT,max}\langle R \rangle$ and $R_{PT,min}/\langle R \rangle$ lie. According to an embodiment of the invention, the bending radius for the fracture test of the entire thin, flat glass article is therefore chosen in such a way that it lies in the range of $R_{min}(s/\langle R \rangle)$, $R_{max}(s/\langle R \rangle)$. In this case, the following relations can be employed for the bending radii $R_{min}(s/\langle R \rangle)$, $R_{max}(s/\langle R \rangle)$:

$$\frac{R_{min}}{\langle R \rangle} = 0.7 + \exp\left(\frac{s}{\langle R \rangle \cdot 0.053} - 2.3\right), \text{ and} \qquad \text{i)}$$

$$\frac{R_{max}}{\langle R \rangle} = 3.4 + \exp\left(\frac{s}{\langle R \rangle \cdot 0.05} - 2.1\right). \qquad \text{ii)}$$

Accordingly, the invention also relates to a method for providing a plate-shaped glass article having high fracture strength, wherein by means of a method according to the inventions for examining the fracture strength of flat samples 10 made of brittle-fracture material, in particular of glass sheets, a plurality of samples 10 (total number N) are used to evaluate the bending radius or tensile stress at which each of the samples 10 breaks, from these values, the mean value $\langle R \rangle$ of the bending radii $R_i$ at which each of the samples (10) has broken is calculated and, using the mean value $\langle R \rangle$, the variance s is calculated according to $$s = \sqrt{\frac{1}{N-1} \sum_{i=1}^{N} (R_i - \langle R \rangle)^2}$$

and wherein then a glass article made of the same glass material as the samples 10, preferably a ribbon of glass (100), is bent in order to test whether the glass article withstands a bending radius $R_{PT}$ or a corresponding tensile stress, wherein the bending radius $R_{PT}$ is chosen in such a way that it lies in the range of the radii $R_{min}$ to $R_{max}$, which are dependent on the relative variance $s/\langle R \rangle$ in this range, wherein the radii $R_{min}$ and $R_{max}$ are given by the above-given Equations i) and ii).

Figure 12:
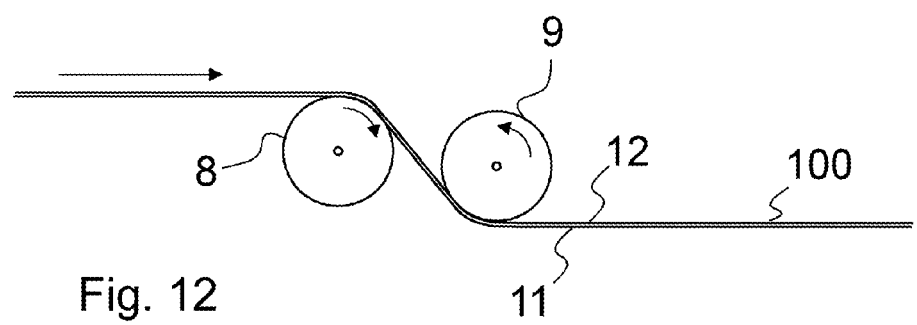
FIG. 12 is a glass article in the form of a ribbon of glass, on which a bend having a bending radius predetermined by rolling is imposed locally.

For this purpose, FIG. 12 shows schematically a glass article in the form of a ribbon of glass 100, which is advanced along the arrow and fed over rolls or rollers 8, 9, so that a bend having a bending radius predetermined by the rollers 8, 9 is imposed locally on the ribbon of glass. The glass article is preferably tested with bends in opposing bending directions. For this purpose, in the example of FIG. 12, the rollers 8, 9 are arranged above and below the ribbon of glass 100, so that the ribbon of glass is bent with each of the two lateral faces 11, 12 around one of the rollers 8, 9.

According to an enhancement, in order to be able to ensure that the entire glass article, which is preferably very large in surface area and elongated, in the form of a ribbon of glass, withstands the bending stress with a bending radius in the range of $R_{min}$ to $R_{max}$, its longitudinal edges are bent along at least % of its total length, preferably along its entire length, at least with the bending radius $R_{PT}$.

As already mentioned, an adjusted random sample can be used for determining the values of <R> (mean value of the bending radius at fracture) and s (variance of the bending radii at fracture), by determining the bending radii or tensile stresses at fracture are determined for at least twenty samples and by discarding the largest and smallest values, preferably 10% of the largest and smallest values, of the bending radius or tensile stress, and by calculating the mean value and the variance by using the remaining values.

The embodiment of the invention described above can then be used to produce a plate-shaped glass article having a guaranteed or predetermined fracture strength under a bending load at a predetermined bending radius, in which the edge thereof or at least one edge of the glass article withstands a bending load with a bending radius $R_{PT}$ along its entire edge length, with the bending radius, corresponding to Equations i), ii) given above, lying in the range of $$R_{min} = \langle R \rangle \cdot \left\{ 0.7 + \exp\left( \frac{s}{\langle R \rangle \cdot 0.053} - 2.3 \right) \right\} \text{ to} \quad \text{iii)}$$

$$R_{max} = \langle R \rangle \cdot \left\{ 3.4 + \exp\left( \frac{s}{\langle R \rangle \cdot 0.05} - 2.1 \right) \right\} \quad \text{iv)}$$

where <R> is the mean value and $$s = \sqrt{\frac{1}{N-1} \sum_{i=1}^{N} (R_i - \langle R \rangle)^2}$$

is the variance of the bending radii at fracture of a plurality of N samples made of the same glass material as the glass material of the glass article, with the bending radii $R_i$ at which each of the samples 10 breaks being determined preferably by means of the method according to the invention for examining the fracture strength of flat samples 10 made of brittle-fracture material.

It is especially preferred that the glass article is a thin ribbon of glass having a length of at least 20 meters, preferably at least 50 meters. Preferably, the ribbon of glass 100 is tested along the entire edge length of at least 20 meters for fracture strength and it is possible to ensure a corresponding bending radius that the ribbon of glass withstands.

The glass article is preferably composed of a lithium aluminum silicate glass, a soda lime silicate glass, a borosilicate glass, an alkali aluminosilicate glass, or an alkali-free or low-alkali aluminosilicate glass. Such glasses are produced, for example, by means of drawing methods, such as a downdraw method, overflow fusion, or by means of float technology.

Advantageously, a low-iron or iron-free glass, in particular one with a $Fe_2O_3$ content less than 0.05 wt %, preferably less than 0.03 wt %, is used, because said glass has reduced absorption and thus makes possible, in particular, an increased transparency. However, for other applications, gray glasses or colored glasses are preferred.

According to an embodiment, a glass or a glass ceramic that is prestressed for its use is used. This glass or glass ceramic can be prestressed chemically by ion exchange or thermally or by a combination of thermal and chemical methods.

An optical glass can also serve as a glass material, such as, for example, a dense flint glass, a lanthanum dense flint glass, a flint glass, a light flint glass, a crown glass, a borosilicate crown glass, a barium crown glass, a dense crown glass, or a fluorine crown glass Advantageously, a low-iron or iron-free glass, in particular one with a $Fe_2O_3$ content of less than 0.05 wt %, preferably of less than 0.03 wt %, can be used, because said glass has reduced absorption and thus, in particular, an increased transparency.

For other applications, however, gray glasses or colored glasses are also preferred.

The invention is suited, in particular, for optimizing the mechanical properties of glasses that are already of high strength. High-strength glasses are typically used for applications in which the glasses are also subjected to a high mechanical load. Such glasses are consequently designed to withstand bending stresses acting on the glass surface area. In this case precisely, the edges of the glasses represent significant weak points. Ultimately, a glass pane made of high-strength glass indeed breaks very quickly if the edge of the pane has flaws and is also subjected to a bending load. It is then possible to examine by means of the invention whether the edges remain constant in their quality when, for instance, individual glass panes are finished by dividing a larger pane. Thus, for example, it is conceivable that, owing to wear, a cutting wheel leaves behind damage at the glass edges. If this is the case, the strength of the entire glass pane is markedly diminished. The method can then be used to determine very precisely such changes in the manufactured product and to test the efficiency of improvements in the formation of edges. Given below are high-strength glasses for which an increase in strength can be achieved by monitoring the edge strength by means of the invention.

Suitable according to an embodiment are glasses having the following constituents, with the molar composition being given in mole percent:

| Constituent | mol % |
| --- | --- |
| $SiO_2$ | 56-70 |
| $Al_2O_3$ | 10.5-16 |
| $B_2O_3$ | 0-3 |
| $P_2O_5$ | 0-3 |
| $Na_2O$ | 10-15 |
| $K_2O$ | 0-2 |
| MgO | 0-3 |
| ZnO | 0-3 |
| $TiO_2$ | 0-2.1 |
| $SnO_2$ | 0-1 |
| F | 0.001-5 |

In addition, it applies as an auxiliary condition that the quotient of the molar content of fluorine to the molar content of $B_2O_3$, that is, $F/B_2O_3$, lies in a range from 0.0003 to 15, preferably from 0.0003 to 11, especially preferably 0.0003 to 10. These glasses can be prestressed chemically and can be used in mobile displays as cover glasses.

The composition in this case preferably contains the following components:

| Component | Mol% |
|---|---|
| $SiO_2$ | 61-70 |
| $Al_2O_3$ | 11-14 |
| $B_2O_3$ | 0-0.5 |
| $Li_2O$ | 0-0.1 |
| $Na_2O$ | 11-15 |
| $K_2O$ | 0-2 |
| MgO | 0-3 |
| CaO | 0 (free) |
| ZnO | 0-1 |
| $CeO_2$ | 0-0.05 |
| $ZrO_2$ | 0 (free) |
| $SnO_2$ | 0-0.3 |
| F | 0.001-3 |
| $F/B_2O_3$ | 0.002-6 |

Especially preferably, the composition contains the following components:

| Component | mol % |
|---|---|
| $SiO_2$ | 64-70 |
| $Al_2O_3$ | 11-14 |
| $B_2O_3$ | 0-0.5 |
| $Li_2O$ | 0-0.1 |
| $Na_2O$ | 11-15 |
| $K_2O$ | 0-2 |
| MgO | 0-3 |
| CaO | 0 (free) |
| ZnO | <0.1 |
| $CeO_2$ | 0-0.05 |
| $ZrO_2$ | 0 (free) |
| $SnO_2$ | 0-0.3 |
| F | 0.001-1 |
| $F/B_2O_3$ | 0.02-2 |

Preferred according to a further development of the invention are borosilicate glasses of the following glass compositions, consisting of (in wt %):

$SiO_2$ 60-85
$Al_2O_3$ 1-10
$B_2O_3$ 5-20
Total $Li_2O+Na_2O+K_2O$ 2-16
Total $MgO+CaO+SrO+BaO+ZnO$: 0-15
Total $TiO_2+ZrO_2$ 0-5
$P_2O_5$ 0-2, as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt %, or, for "black glass," of 0-15 wt %, as well as refining agents such as $As_2O_3$, $Sb_2O_3$, $SnO_2$, $SO_3$, Cl, F, $CeO_2$ of 0-2 wt %.

Alkali-free borosilicate glasses constitute another suitable group of glasses. In this case, the following compositions in weight percent are preferred:

| Component | wt % |
|---|---|
| $SiO_2$ | >58-65 |
| $Al_2O_3$ | >14-25 |
| $B_2O_3$ | >6-10.5 |
| MgO | 0-<3 |
| CaO | 0-9 |
| BaO | >3-8 |
| ZnO | 0-<2 |

These glasses are also described in US 2002/0032117 A1, the content of which is also made the subject of the present application in full scope with respect to glass compositions and glass properties. A glass of this class is marketed by the applicant under the trade name AF32.

The following table lists the contents of components of further alkali-free borosilicate glasses as well as, in the right column, a composition range of a class of glasses having similar properties based on this glass:

| Component | Example wt % | Range (wt %) |
|---|---|---|
| $SiO_2$ | 70 | 67-73 |
| $Al_2O_3$ | 10 | 8-12 |
| $B_2O_3$ | 10 | 8-12 |
| CaO | 6 | 4-9 |
| BaO | 1 | 0.5-2 |
| SrO | 3 | 2-4 |

Yet another class of preferred glass types comprises borosilicate glasses having the following components in weight percent:

| Component | wt % |
|---|---|
| $SiO_2$ | 30-85 |
| $B_2O_3$ | 3-20 |
| $Al_2O_3$ | 0-15 |
| $Na_2O$ | 3-15 |
| $K_2O$ | 3-15 |
| ZnO | 0-12 |
| $TiO_2$ | 0.5-10 |
| CaO | 0-0.1 |

A glass of this class of glasses is the Schott glass D 263. Glasses with more precise compositions are also described in US 2013/207058 A1, the content of which is also made the subject of the present invention in full scope with respect to the compositions of the glasses and the properties thereof.

Soda lime glasses are also suitable. Listed in the following table are two exemplary embodiments and the proportion in weight percent of the components in accordance with a preferred composition range:

|  | Glass 1 | Glass 2 | Range: |
|---|---|---|---|
| $SiO_2$ | 74.42 | 71.86 | 63-81 |
| $Al_2O_3$ | 0.75 | 0.08 | 0-2 |
| MgO | 0.30 | 5.64 | 0-6 |
| CaO | 11.27 | 9.23 | 7-14 |
| $Li_2O$ | 0.00 | 0.00 | 0-2 |
| $Na_2O$ | 12.9 | 13.13 | 9-15 |
| $K_2O$ | 0.19 | 0.02 | 0-1.5 |
| $Fe_2O_3$ | 0.01 | 0.04 | 0-0.6 |
| $Cr_2O_3$ | 0.00 | 0.00 | 0-0.2 |
| $MnO_2$ | 0.00 | 0.00 | 0-0.2 |
| $Co_3O_4$ | 0.00 | 0.00 | 0-0.1 |
| $TiO_2$ | 0.01 | 0.01 | 0-0.8 |

-continued

|  | Glass 1 | Glass 2 | Range: |
|---|---|---|---|
| $SO_3$ | 0.16 | 0.00 | 0-0.2 |
| Se | 0.00 | 0.00 | 0-0.1 |

The glass 2 is especially well suited for the manufacture of sheet glass by the float method.

According to an embodiment, further soda lime silicate glasses of the following compositions are used as glass, consisting of (in wt %):

$SiO_2$ 40-80
$Al_2O_3$ 0-6
$B_2O_3$ 0-5
Total $Li_2O+Na_2O+K_2O$ 5-30
Total $MgO+CaO+SrO+BaO+ZnO$: 5-30
Total $TiO_2+ZrO_2$ 0-7
$P_2O_5$ 0-2,
as well as, if need be, additions of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents such as $As_2O_3$, $Sb_2O_3$, $SnO_2$, $SO_3$, Cl, F, $CeO_2$ of 0-2 wt %.

According to yet another embodiment of the invention, lithium aluminum silicate glasses of the following compositions are used for the glass material, consisting of (in wt %):

$SiO_2$ 55-69
$Al_2O_3$ 19-25
$Li_2O$ 3-5
Total $Na_2O+K_2O$ 0-3
Total $MgO+CaO+SrO+BaO$: 0-5
ZnO 0-4
$TiO_2$ 0-5
$ZrO_2$ 0-3
Total $TiO_2+ZrO_2+SnO_2$ 2-6
$P_2O_5$ 0-8
F 0-1
$B_2O_3$ 0-2,
as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-1 wt %, as well as refining agents such as $As_2O_3$, $Sb_2O_3$, $SnO_2$, $SO_3$, Cl, F, $CeO_2$ of 0-2 wt %.

Further preferred for use as carrier material are alkali aluminosilicate glasses of the following glass compositions, consisting of (in wt %):

$SiO_2$ 40-75
$Al_2O_3$ 10-30
$B_2O_3$ 0-20
Total $Li_2O+Na_2O+K_2O$ 4-30
Total $MgO+CaO+SrO+BaO+ZnO$: 0-15
Total $TiO_2+ZrO_2$ 0-15
$P_2O_5$ 0-10,
as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents such as $As_2O_3$, $Sb_2O_3$, $SnO_2$, $SO_3$, Cl, F, $CeO_2$ of 0-2 wt %.

Further preferably used are alkali-free aluminosilicate glasses of the following glass composition, consisting of (in wt %):

$SiO_2$ 50-75
$Al_2O_3$ 7-25
$B_2O_3$ 0-20
Total $Li_2O+Na_2O+K_2O$ 0-0.1
Total $MgO+CaO+SrO+BaO+ZnO$: 5-25
Total $TiO_2+ZrO_2$ 0-10
$P_2O_5$ 0-5,
as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents such as $As_2O_3$, $Sb_2O_3$, $SnO_2$, $SO_3$, Cl, F, $CeO_2$ of 0-2 wt %.

Further preferably used are low-alkali aluminosilicate glasses of the following glass compositions, composed of (in wt %):

$SiO_2$ 50-75
$Al_2O_3$ 7-25
$B_2O_3$ 0-20
Total $Li_2O+Na_2O+K_2O$ 0-4
Total $MgO+CaO+SrO+BaO+ZnO$: 5-25
Total $TiO_2+ZrO_2$ 0-10
$P_2O_5$ 0-5,
as well as, if need be, additives of coloring oxides, such as, for example, $Nd_2O_3$, $Fe_2O_3$, CoO, NiO, $V_2O_5$, $Nd_2O_3$, $MnO_2$, $TiO_2$, CuO, $CeO_2$, $Cr_2O_3$, rare earth oxides in contents of 0-5 wt % or, for "black glass," of 0-15 wt %, as well as refining agents such as $As_2O_3$, $Sb_2O_3$, $SnO_2$, $SO_3$, Cl, F, $CeO_2$ of 0-2 wt %.

It is possible to use, for example, thin glasses, such as those of Schott A G, Mainz, marketed under the trade names D263, D263 eco, B270, B270 eco, Borofloat, Xensation Cover, Xensation cover 3D, AF45, AF37, AF 32, or AF32 eco.

In another embodiment, the brittle-fracture material is a glass ceramic, in particular in the form of a glass ceramic pane, wherein the glass ceramic consists of a ceramized aluminosilicate glass or a lithium aluminosilicate glass, in particular of a chemically and/or thermally cured, ceramized aluminosilicate glass or lithium aluminosilicate glass. In another embodiment, the brittle-fracture material comprises a ceramizable starting glass, which, in the event of a fire, is ceramized under the action of heat and thereby brings about increased fire protection safety.

Preferably, a glass ceramic or a ceramizable glass having the following composition of the starting glass is used (in wt %):

$Li_2O$ 3.2-5.0
$Na_2O$ 0-1.5
$K_2O$ 0-1.5
Total $Na_2O+K_2O$ 0.2-2.0
MgO 0.1-2.2
CaO 0-1.5
SrO 0-1.5
BaO 0-2.5
ZnO 0-1.5
$Al_2O_3$ 19-25
$SiO_2$ 55-69
$TiO_2$ 1.0-5.0
$ZrO_2$ 1.0-2.5
$SnO_2$ 0-1.0
Total $TiO_2+ZrO_2+SnO_2$ 2.5-5.0
$P_2O_5$ 0-3.0

In another embodiment, a glass ceramic or a ceramizable glass having the following composition is preferably used as the starting glass (in wt %):

Li$_2$O 3-5
Na$_2$O 0-1.5
K$_2$O 0-1.5
Total Na$_2$O+K$_2$O 0.2-2
MgO 0.1-2.5
CaO 0-2
SrO 0-2
BaO 0-3
ZnO 0-1.5
Al$_2$O$_3$ 15-25
SiO$_2$ 50-75
TiO$_2$ 1-5
ZrO$_2$ 1-2.5
SnO$_2$ 0-1.0
Total TiO$_2$+ZrO$_2$+SnO$_2$ 2.5-5
P$_2$O$_5$ 0-3.0

In another embodiment, a glass ceramic or a ceramizable glass having the following composition is preferably used as the starting glass (in wt %):

Li$_2$O 3-4.5
Na$_2$O 0-1.5
K$_2$O 0-1.5
Total Na$_2$O+K$_2$O 0.2-2
MgO 0-2
CaO 0-1.5
SrO 0-1.5
BaO 0-2.5
ZnO 0-2.5
B$_2$O$_3$ 0-1
Al$_2$O$_3$ 19-25
SiO$_2$ 55-69
TiO$_2$ 1.4-2.7
ZrO$_2$ 1.3-2.5
SnO$_2$ 0-0.4
Total TiO$_2$+SnO$_2$ less than 2.7
P$_2$O$_5$ 0-3
Total ZrO$_2$+0.87 (TiO$_2$+SnO$_2$) 3.6-4.3

The glass ceramic preferably contains high-quartz mixed crystals or keatite mixed crystals as predominant crystal phase. The crystallite sizes are preferably smaller than 70 nm, especially preferably smaller than exactly 50 nm, quite especially preferably smaller than exactly 10 nm.

It is obvious to the person skilled in the art that the embodiments described above are to be understood as being given by way of example and that the invention is not limited to them, but rather can be varied in diverse ways without departing from the protective scope of the claims. It is further obvious that the features, independent of whether they are disclosed in the description, the claims, the figures, or otherwise, also define individually essential components of the invention, even if they are described together with other features.

LIST OF REFERENCE NUMBERS 6 frame
7 axis
8, 9 roller
10 sample
10$n$ neutral plane
10$m$ middle of the sample in a two-point bending
11 first lateral face
12 second lateral face
13 margin
13$b$ border
13$p$ margin to be examined
13$s$ end face
131 first corner
132 second corner
15 currently bent section of the sample
16 bend a in circular arc shape
17 examined section of the sample
20 template
21 template surface
23 bending apparatus
24 direction of rotation of the template
28 circle of curvature of the template surface
30 pressing force
31 bendable band/adhesive band
31$a$ protruding end of the band
31$b$ protruding end of the band
32 tensile force
33 feeding device
34 direction of feeding
41 near-margin defect of the sample
42 crack
51, 52 support plates
100 ribbon of glass
103 roll of glass
104 inner side 104 of 103
107 sheeting material
300 step roller
300$p$ point of contact of the surface projections
301-320 discs of the step roller

What is claimed is:

1. A method for examining the fracture strength of a flat sample made of brittle-fracture material, comprising:
providing in the flat sample having a first lateral face, a second lateral face, and at least one margin, the first lateral face lying opposite to the second lateral face;
pressing a section of the flat sample against a template surface of a dimensionally stable template having a defined curvature so that the defined curvature of the template surface is imposed on the section so that the section is subjected to a tensile stress o along the at least one margin;
repeating the pressing step with template surfaces having successively reduced bending radii until the flat sample breaks; and
evaluating a tensile stress o or at which bending radius the flat sample has broken.

2. The method according to claim 1, wherein the defined curvature is a circular arc shape with a bending radius (R).

3. The method according to claim 2, further comprising displacing the flat sample lengthwise along the at least one margin continuously or stepwise relative to the template surface between each pressing step.

4. The method according to claim 2, wherein the bending radius (R) lies in an interval between a lower value $R_{min}$ and an upper value $R_{max}$, so that $$R_{min} \leq R \leq R_{max}, \text{ where}$$

$$R_{min} = E*t/(2*o*(1-f)) \text{ and}$$

$$R_{max} = E*t/(2*o*(1+f)) \text{ and}$$

where E stands for the modulus of elasticity of the sample material, o stands for a predetermined tensile stress, and f is a number between 0 and 1.

5. The method according to claim 2, wherein the template surface is a cylinder and the bending radius (R) is a constant radius $R_L$.

6. The method according to claim 2, wherein the template surface is a cone with a cross section of circular arc shape and the bending radius (R) is a constant radius $R_L$ at least at one point.

7. The method according to claim 6, wherein the circular arc shape is concave, and wherein the pressing step comprises pressing the section of the first lateral face flatly and radially against the template surface so that the section is in flat contact with the concave template surface.

8. The method according to claim 6, wherein the circular arc shape is convex, and wherein the pressing step comprises pressing the section of the second lateral face flatly and radially against the template surface so that the section is in flat contact with the convex template surface.

9. The method according to claim 8, wherein the pressing further comprises transmitting a pressing force from a bendable band to the first lateral face or the second lateral face.

10. The method according to claim 8, wherein the pressing further comprises adhesively attaching a bendable band to the first lateral face or the second lateral face parallel to the at least one margin and distanced from the at least one margin.

11. The method according to claim 1, wherein the at least one margin is a lengthwise edge.

12. The method according to claim 1, wherein the pressing further comprises:
    pressing the first lateral face against the template surface;
    rotating the flat sample and template surface with respect to one another; and
    pressing the second lateral face against the template surface.

13. A method for examining the fracture strength of a flat sample made of brittle-fracture material, comprising:
    providing in the flat sample having a first lateral face, a second lateral face, and at least one margin, the first lateral face lying opposite to the second lateral face;
    pressing a section of the flat sample against a template surface of a dimensionally stable template having a defined curvature so that the defined curvature of the template surface is imposed on the section so that the section is subjected to a tensile stress o along the at least one margin;
    repeating the pressing step with template surfaces having successively reduced bending radii until the flat sample breaks;
    evaluating a tensile stress o or at which bending radius the flat sample has broken;
    evaluating the tensile stress o or the bending radius at which a plurality of flat samples has broken;
    calculating, from the tensile stress o or the bending radius, a mean value <R> of a bending radii $R_i$; and
    calculating a variance s is calculated according to $$s = \sqrt{\frac{1}{N-1}\sum_{i=1}^{N}(R_i - \langle R \rangle)^2}.$$

14. The method according to claim 13, further comprising:
    making a glass article of the same glass material as the plurality of flat samples;
    bending the glass article to a bending radius $R_{PT}$, the bending radius $R_{PT}$ being chosen so that it lies in the range of the radii $R_{min}$ to $R_{max}$, which are dependent on the relative variance s/<R>, wherein the radii $R_{min}$ and $R_{max}$ are given by the equations $$\frac{R_{min}}{\langle R \rangle} = 0.7 + \exp\left(\frac{s}{\langle R \rangle \cdot 0.053} - 2.3\right), \text{ and}$$

$$\frac{R_{max}}{\langle R \rangle} = 3.4 + \exp\left(\frac{s}{\langle R \rangle \cdot 0.05} - 2.1\right).$$

15. The method according to claim 14, further comprising bending the glass article in opposing bending directions.

16. A plate-shaped glass article having a predetermined fracture strength under a bending load with a predetermined bending radius, wherein at least one edge of the glass article withstands a bending load with a bending radius $R_{PT}$ along its entire edge length, wherein the bending radius lies in the range of $$R_{min} = \langle R \rangle \cdot \left\{0.7 + \exp\left(\frac{s}{\langle R \rangle \cdot 0.053} - 2.3\right)\right\} \text{ to}$$

$$R_{max} = \langle R \rangle \cdot \left\{3.4 + \exp\left(\frac{s}{\langle R \rangle \cdot 0.05} - 2.1\right)\right\}$$

where <R> is the mean value and $$s = \sqrt{\frac{1}{N-1}\sum_{i=1}^{N}(R_i - \langle R \rangle)^2}$$

is the variance of the bending radii at fracture of a plurality N of samples made of the same glass material as the glass material of the glass article, wherein the bending radii $R_i$ at which each of the samples breaks.

17. The plate-shaped glass article according to claim 16, wherein the glass article is a thin ribbon of glass having a length of at least 20 meters.

18. An apparatus for examining the fracture strength of flat samples made of brittle-fracture material, comprising:
    a bending device for imposing a homogenous, convex bend of circular arc shape on a sample having a first lateral face, a second lateral face, and at least one margin, the at least one margin forming a transition of the first lateral face to the second lateral face and the sample having a thickness t at the at least one margin;
    a template having a template surface with the bend of circular arc shape, wherein the template is a multiple template having a cylinder or cylinder section so that the template surface has cross sections of the circular arc shape with different radii; and
    a pressing device for flat pressing of the first lateral face or of the second lateral face against the template surface with a pressing force running radially to the template.

19. The apparatus according to claim 18, further comprising a feeding device configured to advancing the flat samples along the at least one margin relative to the template.

20. A multiple template for determining the mechanical tensile stress at break $\sigma_b$ of flat samples made of brittle-fracture material, comprising:
    at least four templates for examining the fracture strength of samples, each of the at least four templates having a template surface that is dimensionally stable and is designed as a convex cylinder, each of the at least four templates having a radius $R_i$, where i is a number between 0 and (N−1) and where N is the number of templates of the multiple template, and wherein the template radii $R_i$ differ between the templates with the following relationship:

$$R_{i+1} < R_i \text{ for } i=0 \text{ to } i=(N-2), \text{ and}$$

$$R_{i,min} < R_i < R_{i,max},$$

where $$R_{i,min} = R_{i,q} * (p*q)^{\wedge(-1/2)} \text{ and}$$

$$R_{i,max} = R_{i,q} * (p*q)^{\wedge(+1/2)},$$

and where
$R_{i,q} = R_0 * q^{\wedge(-i)}$ corresponds to a geometric series with a multiplication factor q and
where this multiplication factor is $$q = (\sigma_{max}/\sigma_{min})^{\wedge(1/(N-1))} = (R_{N-1}/R_0)^{\wedge(1/(N-1))} \text{ and}$$

p is a real number between 0 and 1.

21. A multiple template for examining the fracture strength of a plurality of flat samples made of brittle-fracture material, comprising:
a plurality of templates for examining the flat samples having a thicknesses $t_i$, where i is a whole number between 1 and N and where N is the number of templates of the plurality of templates, wherein each template has a dimensionally stable template surface, and the template surface is a convex cylinder with a radius $R_i$, wherein the following relation applies to these radii:

$$R_{i+1} < R_i \text{ for } 0 < i < N-1, \text{ and}$$

the radii $R_i$ of the plurality of templates are different and deviate by no more than 30% from reference values, wherein the reference values are chosen from the set {C*20 μm, C*25 μm, C*30 μm, C*50 μm, C*70 μm, C*100 μm, C*145 μm, C*200 μm}, where C is a constant.

22. The multiple template according to claim 21, wherein $C = E/(2*\sigma)$, where E is the modulus of elasticity of the sample material, and o is the tensile stress under which the samples are to be examined.

* * * * *